US012747280B2

(12) United States Patent
Sen Gupta et al.

(10) Patent No.: US 12,747,280 B2
(45) Date of Patent: Sep. 29, 2026

(54) NEUTROPHIL ELASTASE BINDING PEPTIDES AND COMPOSITIONS THEREOF

(71) Applicants: CASE WESTERN RESERVE UNIVERSITY, Cleveland, OH (US); The United States Government as Represented by the Department of Veteran Affairs, Washington, DC (US)

(72) Inventors: Anirban Sen Gupta, Cleveland, OH (US); Evi Stavrou, Cleveland, OH (US)

(73) Assignees: CASE WESTERN RESERVE UNIVERSITY, Cleveland, OH (US); THE UNITED STATES AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 976 days.

(21) Appl. No.: 17/793,545

(22) PCT Filed: Jan. 19, 2021

(86) PCT No.: PCT/US2021/013965
§ 371 (c)(1),
(2) Date: Jul. 18, 2022

(87) PCT Pub. No.: WO2021/146715
PCT Pub. Date: Jul. 22, 2021

(65) Prior Publication Data

US 2023/0235022 A1 Jul. 27, 2023

Related U.S. Application Data

(60) Provisional application No. 62/961,999, filed on Jan. 16, 2020.

(51) Int. Cl.

| | |
|---|---|
| ***A61K 38/00*** | (2006.01) |
| ***A61K 47/62*** | (2017.01) |
| ***A61K 47/69*** | (2017.01) |
| ***A61P 9/14*** | (2006.01) |
| ***A61P 35/00*** | (2006.01) |
| ***C07K 7/08*** | (2006.01) |
| ***C07K 14/81*** | (2006.01) |

(52) U.S. Cl.
CPC ........ *C07K 14/811* (2013.01); *A61K 47/6911* (2017.08); *A61P 35/00* (2018.01)

(58) Field of Classification Search
CPC .... A61K 38/00; A61K 47/62; A61K 47/6911; A61K 47/6913; A61P 35/00; A61P 9/14; C07K 14/811; C07K 14/8114; C07K 14/8125; C07K 7/08; C12Y 304/21037
See application file for complete search history.

(56) References Cited

U.S. PATENT DOCUMENTS

| | | | | |
|---|---|---|---|---|
| 9,107,963 | B2 | 8/2015 | Sen Gupta et al. | |
| 2006/0217294 | A1 * | 9/2006 | Appeldoorn | A61P 35/02 514/19.8 |
| 2010/0144630 | A1 | 6/2010 | Shapiro | |
| 2012/0094931 | A1 | 4/2012 | Collins et al. | |

FOREIGN PATENT DOCUMENTS

| | | | |
|---|---|---|---|
| WO | 92/18141 | A1 | 10/1992 |
| WO | 2001/34640 | A2 | 5/2001 |
| WO | 2011/050098 | A2 | 4/2011 |
| WO | 2012/012146 | A2 | 4/2012 |
| WO | 2015/006228 | A1 | 1/2015 |

OTHER PUBLICATIONS

Filpula et al., "Releasable PEGylation of proteins with customized linkers," Advanced Drug Delivery Reviews, 2008, 60: 29-49. (Year: 2008).*

European Application No. 21741315.2, Extended Search Report dated Jan. 15, 2024.

Chung, Hye-Shin, "Role of the P2 residue of human alpha 1-antitrypsin in determining target protease specificity" PLOS ONE, Sep. 18, 2017, pp. 1-12.

Japanese Application No. 2022-543430, Office Action dated Jan. 21, 2025.

Applicant: Case Western Reserve University; "Neutrophil Elastase Binding Peptides and Compositions Thereof"; International Application No. PCT/US21/13965 Filed: Jan. 19, 2021; PCT International Search Report mailed: Jun. 9, 2021; 5 pgs.

* cited by examiner

*Primary Examiner* — Julie Ha
(74) *Attorney, Agent, or Firm* — Tarolli, Sundheim, Covell & Tummino LLP

(57) ABSTRACT

A therapeutic or diagnostic composition includes nanoparticle or microparticle constructs designed to target activated neutrophils. Each construct features an outer surface conjugated with multiple targeting peptides. These targeting peptides comprise an amino acid sequence with at least 60% identity to SEQ ID NO: 1 or a retro-inverso amino acid sequence thereof, modified by a substitution at position 4P, 5M, or 6S. The modified peptides facilitate specific binding to neutrophil elastase present on the surface of neutrophils, allowing for site-specific delivery or monitoring of the constructs in inflammatory environments.

18 Claims, 18 Drawing Sheets

Specification includes a Sequence Listing.

Fig. 3A-B i NT-NP binding on h-NE a NT-NP binding to activated neutrophil g Colocalization of NP with neutrophils *in vivo* h Quantification of NP-neutrophil colocalization

| Condition | Manders' M1 | Manders' M2 |
|---|---|---|
| U-NP + No LPS | 0 | 0 |
| NT-NP + No LPS | 0 – 0.005 | 1 |
| U-NP + LPS | 0.006 – 0.05 | 1 |
| NT-NP + LPS | 0.83 - 1 | 0.88 - 1 |

NEUTROPHIL ELASTASE BINDING PEPTIDES AND COMPOSITIONS THEREOF

RELATED APPLICATION

This application claims priority from U.S. Provisional Application No. 62/961,999, filed Jan. 16, 2020, the subject matter of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 19, 2021, is named CWR028113WOORDSEQUENCELISTING.txt and is 14,309 bytes in size.

TECHNICAL FIELD

This application relates to neutrophil elastase binding or targeting peptides and to the use of these neutrophil elastase binding or targeting peptides in nanoparticle and/or microparticle compositions for diagnostic and therapeutic applications.

BACKGROUND

Neutrophils play key roles in the development and progression of many inflammatory diseases where inflammation becomes detrimental. Such diseases include chronic obstructive pulmonary disease (COPD), systemic lupus erythematosous, vasculitis, diabetic wound healing, venous and arterial thrombosis, and cancer. For example, elevated levels of neutrophils (reaching about 70% of the total inflammatory cells) and a 5- to 10-fold increase in macrophages are found in sputum and bronchial lavage samples from COPD patients. In many inflammatory diseases, the extent of neutrophilic infiltrates correlates with disease activity and symptoms, and underlies the pathophysiology. To treat and manage sterile inflammation, potent immunosuppressants, such as steroids, are commonly employed. Due to the lack of specificity, a range of considerable side-effects may occur including significant psychiatric and systemic metabolic disturbances in many patients. Thus, methods that afford selective targeting of anti-inflammatory agents to the specific cell types of interest, such as neutrophils, are needed.

Nanotechnology is playing an important role in providing new types of therapeutic interventions. Systemically administered nanotherapeutics have shown to enhance the therapeutic index of drugs (especially anticancer agents), either by increasing the drug concentration at the site of interest and/or by decreasing the exposure in healthy tissues. Nanoscale delivery systems offer the potential of multifunctional platforms due to their ability to (i) carry large “payloads” of one or more types of drugs for therapy or contrast agents for imaging or combinations of drugs and contrast agents and (ii) manipulate pharmacokinetics and biodistribution of systemically administered agents. Nanocarriers can theoretically be designed to passively and actively target sites of interest. Passive targeting results from prolonged circulation of nanocarriers allowing for accumulation at sites with abnormal, leaky vasculature, such as cancerous and inflamed tissues. This preferential accumulation, termed the enhanced permeation and retention (EPR) effect, occurs due to passive convective transport through leaky endothelium.

Since the convective transport of these particles far outweighs the diffusive component, the particles do not generally return to the blood stream, in contrast to small molecules. To further increase the targeting affinity and selectivity, nanocarriers can be tagged with targeting molecules (e.g., peptides, antibodies) that bind to specific-targeting receptors that are expressed on cells of interest for active targeting.

SUMMARY

Embodiments described herein relate to peptides that bind to or target neutrophil elastase and to their use in therapeutic and diagnostic applications. The neutrophil elastase binding peptides or targeting peptides can have an amino acid sequence substantially identical to an about 5 to about 20, about 6 to about 19, about 7 to about 18, about 8 to about 17, about 9 to about 16, about 10 to about 15, or about 11 to about 14 consecutive amino acid sequence reactive center loop (RCL) portion of alpha-1 anti-trypsin (AAT) that is responsible for binding to and inactivating neutrophil elastase bound on the surface of activated neutrophils or a retro-inverso amino acid sequence of the amino acid sequence thereof.

The RCL portion of AAT includes a Met358-Ser359 bond that is highly stressed and cleaved by neutrophil elastase upon binding of AAT to neutrophil elastase. Cleavage of AAT’s reactive center loop, releases stored potential energy and results in a conformational change in which neutrophil elastase is flipped to the opposite end of the AAT molecule. In the process, NE is distorted and catalytically inactivated. Advantageously, unlike the RCL portion of AAT that binds to NE, the neutrophil elastase binding peptides described herein are either not cleaved by NE or their sequential, high-affinity binding results in sustained interactions with NE and thus binding of the neutrophil elastase binding peptides or nanoparticles and/or microparticles coupled thereto with NE can be sustained, as opposed to short-lived, to provide sustained binding of the neutrophil elastase binding peptides or nanoparticles and/or microparticles coupled thereto to the NE and neutrophils.

In some embodiments, a peptide that binds to or targets neutrophil elastase on the surface of activated neutrophils can include about 5 to about 20, about 6 to about 19, about 7 to about 18, about 8 to about 17, about 9 to about 16, about 10 to about 15, or about 11 to about 14 acid sequence that is at least about 60%, at least about 70%, at least about 80%, or at least about 90% identical to an about 5 to about 20, about 6 to about 19, about 7 to about 18, about 8 to about 17, about 9 to about 16, about 10 to about 15, or about 11 to about 14 consecutive amino acid sequence reactive center loop (RCL) portion of alpha-1 antirypsin (AAT) that is responsible for binding to and inactivating neutrophil elastase and that includes the Met358-Ser359 bond or a retro-inverso amino acid sequence of the amino acid sequence thereof. In some embodiments, the binding of the neutrophil elastase binding peptides or nanoparticles and/or microparticles coupled thereto can be sustained, as opposed to short-lived, to provide sustained binding of the neutrophil elastase binding peptides or nanoparticles and/or microparticles coupled thereto to the NE and neutrophils.

In some embodiments, the neutrophil elastase binding peptide can include an amino acid sequence that is at least about 60%, at least about 70%, at least about 80%, or at least about 90% identical to an amino acid sequence of EAIPMSIPPEVK (SEQ ID NO: 1) or a retro-inverso amino acid sequence of SEQ ID NO: 1, wherein the peptide binds NE.

For example, the neutrophil elastase binding peptide can include a substitution of an amino acid of at least one of residue 4P, 5M, or 6S of EAIPMSIPPEVK (SEQ ID NO: 1).

In other embodiments, the neutrophil elastase binding peptide can include an amino acid sequence of EAI$X_1X_2X_3$IPPEVK (SEQ ID NO: 2) or a retro-inverso amino acid sequence of SEQ ID NO: 2, wherein $X_1$ is P, A, S, N, or L, $X_2$ is A, C, D, E, F, G, H, I, K, L, M, N, P, Q, R, S, T, W, or Y, and $X_3$ is S or A.

In some embodiments, $X_2$ is M, if at least one of $X_1$ or $X_3$ is not S.

In other embodiments, $X_1$ is not P if $X_2$ is M and $X_3$ is S.

In still other embodiments, $X_2$ is not M if $X_1$ is P and $X_3$ is S.

In other embodiments, $X_3$ is not S if $X_1$ is P and $X_2$ is M.

In some embodiments, the neutrophil elastase binding peptide can include an amino acid sequence selected from the group consisting of:

| | |
|---|---|
| EAIPMAIPPEVKF, | (SEQ ID NO: 3) |
| EAIPVSIPPEVKF, | (SEQ ID NO: 4) |
| EAIPASIPPEVKF, | (SEQ ID NO: 5) |
| EAIPCSIPPEVKF, | (SEQ ID NO: 6) |
| EAIPDSIPPEVKF, | (SEQ ID NO: 7) |
| EAIPESIPPEVKF, | (SEQ ID NO: 8) |
| EAIPFSIPPEVKF, | (SEQ ID NO: 9) |
| EAIPGSIPPEVKF, | (SEQ ID NO: 10) |
| EAIPHSIPPEVKF, | (SEQ ID NO: 11) |
| EAIPISIPPEVKF, | (SEQ ID NO: 12) |
| EAIPKSIPPEVKF, | (SEQ ID NO: 13) |
| EAIPLSIPPEVKF, | (SEQ ID NO: 14) |
| EAIPNSIPPEVKF, | (SEQ ID NO: 15) |
| EAIPPSIPPEVKF, | (SEQ ID NO: 16) |
| EAIPQSIPPEVKF, | (SEQ ID NO: 17) |
| EAIPRSIPPEVKF, | (SEQ ID NO: 18) |
| EAIPSSIPPEVKF, | (SEQ ID NO: 19) |
| EAIPTSIPPEVKF, | (SEQ ID NO: 20) |

-continued

| | |
|---|---|
| EAIPWSIPPEVKF, | (SEQ ID NO: 21) |
| EAIPYSIPPEVKF, | (SEQ ID NO: 22) |
| EAIAMSIPPEVKF, | (SEQ ID NO: 23) |
| EAISMSIPPEVKF, | (SEQ ID NO: 24) |
| EAINMSIPPEVKF, | (SEQ ID NO: 25) |
| EAILMSIPPEVKF, | (SEQ ID NO: 26) |
| EAIAMAIPPEVKF, | (SEQ ID NO: 27) |
| EAISMAIPPEVKF, | (SEQ ID NO: 28) |
| EAINMAIPPEVKF, | (SEQ ID NO: 29) |
| EAILMAIPPEVKF, | (SEQ ID NO: 30) |
| EAIPMAIPPEVK, | (SEQ ID NO: 31) |
| EAIPVSIPPEVK, | (SEQ ID NO: 32) |
| EAIPASIPPEVK, | (SEQ ID NO: 33) |
| EAIPCSIPPEVK, | (SEQ ID NO: 34) |
| EAIPDSIPPEVK, | (SEQ ID NO: 35) |
| EAIPESIPPEVK, | (SEQ ID NO: 36) |
| EAIPFSIPPEVK, | (SEQ ID NO: 37) |
| EAIPGSIPPEVK, | (SEQ ID NO: 38) |
| EAIPHSIPPEVK, | (SEQ ID NO: 39) |
| EAIPISIPPEVK, | (SEQ ID NO: 40) |
| EAIPKSIPPEVK, | (SEQ ID NO: 41) |
| EAIPLSIPPEVK, | (SEQ ID NO: 42) |
| EAIPNSIPPEVK, | (SEQ ID NO: 43) |
| EAIPPSIPPEVK, | (SEQ ID NO: 44) |
| EAIPQSIPPEVK, | (SEQ ID NO: 45) |
| EAIPRSIPPEVK, | (SEQ ID NO: 46) |
| EAIPSSIPPEVK, | (SEQ ID NO: 47) |

-continued (SEQ ID NO: 48)
EAIPTSIPPEVK, (SEQ ID NO: 49)
EAIPWSIPPEVK, (SEQ ID NO: 50)
EAIPYSIPPEVK, (SEQ ID NO: 51)
EAIAMSIPPEVK, (SEQ ID NO: 52)
EAISMSIPPEVK, (SEQ ID NO: 53)
EAINMSIPPEVK, (SEQ ID NO: 54)
EAILMSIPPEVK, (SEQ ID NO: 55)
EAIAMAIPPEVK, (SEQ ID NO: 56)
EAISMAIPPEVK, (SEQ ID NO: 57)
EAINMAIPPEVK, (SEQ ID NO: 58))
EAILMAIPPEVK, and retro-inverso amino acid sequences of SEQ ID Nos: 1-58.

In other embodiments, the neutrophil elastase binding peptide can include an amino acid linker to link the neutrophil elastase binding peptide to another peptide, molecule, or compound. For example, the linker can include CG residues linked to the 1E residue of the amino acid sequence of EAIPMSIPPEVK (SEQ ID NO: 1) or EAIPMSIPPEVKF (SEQ ID NO: 59).

Other embodiments described herein relate to a composition that includes a plurality of nanoparticle and/or microparticle constructs that target activated neutrophils. Each nanoparticle and/or microparticle construct can have an outer surface and a plurality of neutrophil elastase binding peptides conjugated to the surface of the nanoparticle and/or microparticle construct. The neutrophil elastase binding peptides can include an amino acid sequence as described herein. In some embodiments, the neutrophil elastase binding peptides can bind neutrophil elastase on the neutrophil surface and are either not cleaved by neutrophil elastase or their sequential high-affinity binding onto NE rendered by multiple targeting peptides on nanoparticles, ensures sustained interaction with neutrophil elastase.

In some embodiments, the nanoparticle and/or microparticle construct can include, for example, a liposome, a lipidic nanoparticle or microparticle, a hydrogel nanoparticle or microparticle, a micelle, a metal nanoparticle, a polymer nanoparticle, a dendrimer, quantum dot, and/or combinations of these materials.

In other embodiments, the nanoparticle and/or microparticle construct can further include a therapeutic agent. The therapeutic agent can be encapsulated by and/or conjugated to the nanoparticle and/or microparticle construct.

In some embodiments, the therapeutic agent can include NET-dissolving agents, such as DNAse, NET preventing agents, such as PAD-4 inhibitors, Akt-1 and Akt-2 phosphorylation inhibitors, inflammasome inhibitors, TLR 4 inhibitors, autophagy inhibitors, such as hydroxychloroquine (HCQ), heme quenchers, such as hemopexin, inhibitors of neutrophil FXII-uPAR interactions, and anticoagulant agents, such as heparin, enoxaparin, thrombin inhibitors, and other coagulation factor inhibitors.

In some embodiments, the neutrophil elastase binding peptides can be spatially or topographically arranged on surfaces of the nanoparticle and/or microparticle constructs such that the neutrophil elastase binding peptides do not spatially mask each other.

In other embodiments, the nanoparticle and/or microparticle constructs can include other targeting or binding moieties or agents, such as targeting peptides, antibodies, antigen binding fragments thereof, and carbohydrate ligands, conjugated to surfaces of the nanoparticle and/or microparticle constructs besides the neutrophil elastase binding peptides described herein. The other targeting moieties can include, for example, platelet targeting peptides, fibrin binding peptides, endothelium targeting agents, cancer cell targeting agents, and immune cell targeting peptides. In some embodiments, the platelet targeting peptide can include a GPIIb-IIIa-binding peptide, such as a fibrinogen-mimicking peptide, GPIb binding peptide, such as a vWF-mimicking peptide, and/or a P-selectin binding peptide. The endothelium targeting agents can target inflamed endothelium surface molecules and include antibodies, peptides or carbohydrate ligands directed to various cell adhesion molecules, such as ICAM, VCAM, PCAM, as well as integrins, such as $\alpha M\beta 3$ and $\alpha 5\beta 1$, and other lectins, such as E-selectin and L-selectin. The cancer cell targeting agents can include peptides or antibodies that target or bind to PSMA, EGFR, Transferrin Receptor, HER-2 receptor, and/or Folate receptor.

In some embodiments, a composition including the nanoparticle and/or microparticle constructs and the neutrophil elastase binding peptides described herein can be used in a method of treating diseases caused by neutrophil activation and/or inflammatory diseases accompanied by neutrophil activation. The diseases caused by neutrophil activation and/or the inflammatory diseases accompanied by neutrophil activation can be one or a plurality of diseases selected from venous and arterial thrombosis, deep vein thrombosis and vascular thrombo-embolism (DVT+VTE), lupus, psoriasis, atherosclerosis, endometriosis, trauma, sickle cell disease associated acute chest syndrome and pulmonary thrombosis, immunothrombosis, thrombo-inflammation, chronic and diabetic wounds, sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cancer, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, Kawasaki disease, multiple sclerosis, diabetic vascular complication, diabetic wounds, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, hemodialysis, extracorporeal circulation, artificial breathing, acute/chronic rejection after organ transplantation, SLE, rheumatoid arthritis, DIC, autoimmune disease group, Bechet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

DETAILED DESCRIPTION

Figure 1:
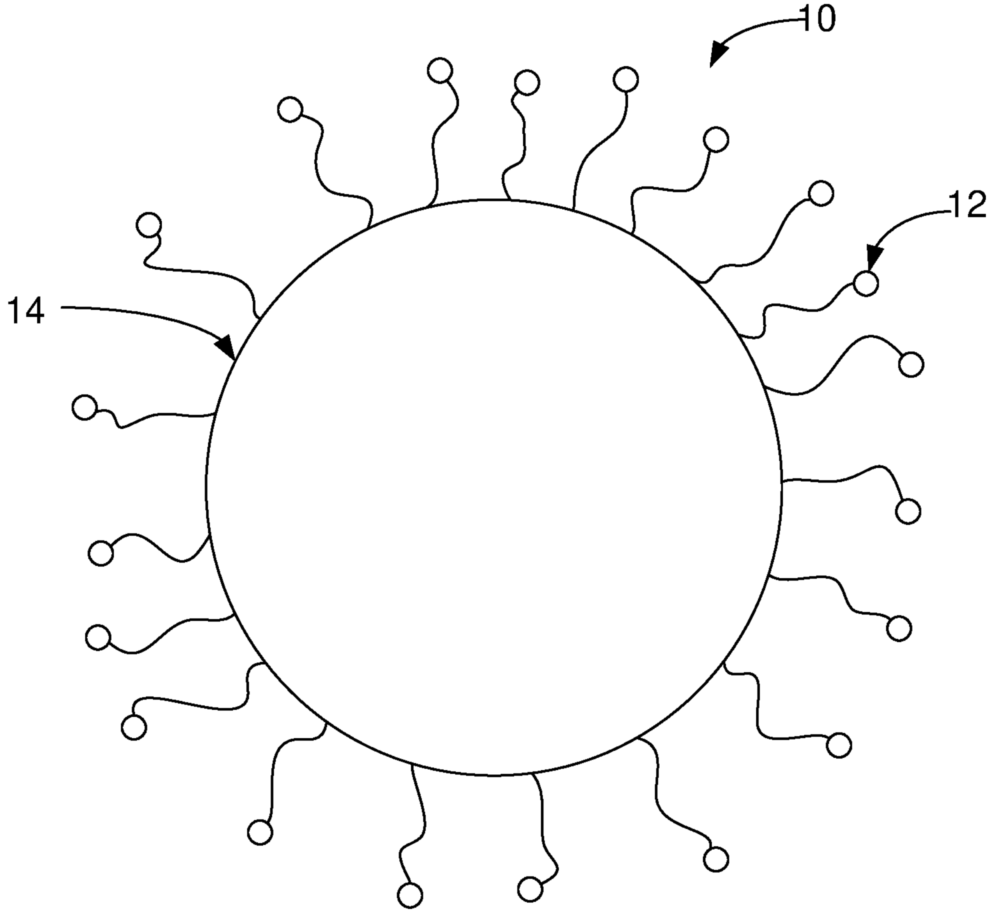
FIG. 1 is a schematic illustration showing the design of a liposomal construct surface-functionalized with neutrophil elastase binding peptides.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, aves, etc.).

The terms "diminishing," "reducing," or "preventing," "inhibiting," and variations of these terms, as used herein include any measurable decrease, including complete or substantially complete inhibition. The terms "enhance" or "enhanced" as used herein include any measurable increase or intensification.

As used herein, the term "small molecule" can refer to lipids, carbohydrates, polynucleotides, polypeptides, or any other organic or inorganic molecules.

As used herein, the term "polypeptide" refers to a polymer composed of amino acid residues related naturally occurring structural variants, and synthetic non-naturally occurring analogs thereof linked via peptide bonds or modified peptide bonds (i.e., peptide isosteres), related naturally occurring structural variants, and synthetic non-naturally occurring analogs thereof, glycosylated polypeptides, and all "mimetic" and "peptidomimetic" polypeptide forms. Synthetic polypeptides can be synthesized, for example, using an automated polypeptide synthesizer. The term can refer to an oligopeptide, peptide, polypeptide, or protein sequence, or to a fragment, portion, or subunit of any of these. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "portion" of a polypeptide or protein means at least about three sequential amino acid residues of the polypeptide. It is understood that a portion of a polypeptide may include every amino acid residue of the polypeptide.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

As used herein, the term "imaging agent" can refer to a biological or chemical moiety capable of be encapsulated by a nanoparticle or microparticle construct of the application and that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to increase blood flow by a measurable amount from a thrombosed value. Thus, "treating" or "treatment" does not require complete restoration of blood flow from a thrombosed value.

As used herein, the term "targeting moiety" or "targeting agent" can refer to a molecule or molecules that are able to bind to and complex with a biomarker. The term can also refer to a functional group that serves to target or direct a therapeutic agent to a particular location, cell type, diseased tissue, or association. In general, a "targeting moiety" or "targeting agent" can be directed against a biomarker.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. "Therapeutic agents" can include any agent (e.g., molecule, drug, pharmaceutical composition, etc.) capable of be encapsulated by a nanoparticle or microparticle construct of the application and further capable of preventing, inhibiting, or arresting the symptoms and/or progression of a disease.

"Nanoparticle" or "microparticle" as used herein is meant to include particles, spheres, capsules, and other structures having a length or diameter of about 10 nm to about 100 μm. For the purposes of this application, the terms "nanosphere", "nanoparticle", "nanoparticle construct", "nanovehicle", "nanocapsule", "microsphere", "microparticle", and "microcapsule" are used interchangeably.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

Embodiments described herein relate to peptides that bind to or target neutrophil elastase (NE) and to their use in therapeutic and diagnostic applications. The NE targeting peptides can be used in diagnostic, therapeutic, and/or theranostic applications to deliver therapeutic agents and/or imaging agents to activated neutrophils and/or nearby tissues in a subject as well as selectively target activated neutrophils and/or tissue of a subject upon systemic administration (e.g., intravenous, intravascular, intraarterial infusion) of compositions comprising the peptides to the subject.

The peptides or compositions described herein include targeting or binding peptides to NE, which are bound to the surface of activated neutrophils. NE is one of several hydrolytic enzymes contained in the azurophil granules of human and murine neutrophils. Physiologically, it is involved in the degradation of foreign material ingested during phagocytosis. NE has also been implicated in abnormal lung connective tissue turnover and is also responsible, at least in part, for sterile thrombo-inflammatory conditions and delayed wound healing. The activity of NE is strictly regulated to avoid uncontrolled proteolysis and inflammation in the body by (1) channeling into specialized compartments (e.g., storage in azurophil granules in the cytoplasm of neutrophils), and (2) by extracellular neutralizing, endogenous serine protease inhibitors (SERPINs), primarily, alpha-1 antitrypsin (AAT). However, a portion of secreted NE remains bound on the neutrophil surface and is catalytically active. At the site of secretion, the mM concentration of NE outcompetes the μM concentration of extracellular antiproteases. As a result, only a small space of obligate NE activity exists that is found on activated neutrophils.

The neutrophil elastase binding peptides described herein have an amino acid sequence substantially identical to an about 5 to about 20, about 6 to about 19, about 7 to about 18, about 8 to about 17, about 9 to about 16, about 10 to about 15, or about 11 to about 14 consecutive amino acid sequence reactive center loop (RCL) portion of alpha-1 anti-trypsin (AAT) that is responsible for binding to and inactivating neutrophil elastase bound on the surface of activated neutrophils or a retro-inverso amino acid sequence of the amino acid sequence thereof. The fully processed mature AAT protein is a 394-amino acid peptide, 52 kDa in size. The crystal structure of AAT revealed a 6.7 nm×3.2 nm globular protein with three carbohydrate side chains on the outer surface, localized to one end. The AAT polypeptide chain is arranged into well-defined structural elements consisting of three beta-sheets (A-C) and nine alpha-helices (A-I), each formed by the first 150 residues. There are three internal salt bridges occurring within the molecule that have been implicated in folding and polymerization. At the active site, a Met358-Ser359 bond is part of a highly stressed reactive center loop that if cleaved separates the two residues widely exposing the N-terminal region of the active site loop on two strands of beta-sheet A. It is this active site, which is responsible for the functional capacity of the inhibitor as well as its specificity. Upon binding, NE cleaves AAT's reactive center loop, releasing stored potential energy and resulting in a conformational change in which NE is flipped to the opposite end of the AAT molecule. In the process, NE is distorted and catalytically inactivated. In some embodiments, unlike the RCL portion of AAT that binds to NE, the neutrophil elastase binding peptides described herein can be modified such that they are not cleaved or not rapidly cleaved by the NE and, thus, binding of the neutrophil elastase binding peptide with NE is sustained compared native ATT or peptides having native AAT-RCL amino acid sequences.

In some embodiments, a peptide that binds to or targets neutrophil elastase on the surface of activated neutrophils can include about 5 to about 20, about 6 to about 19, about 7 to about 18, about 8 to about 17, about 9 to about 16, about 10 to about 15, or about 11 to about 14 acid sequence that is at least about 60%, at least about 70%, at least about 80%, or at least about 90% identical to an about 5 to about 20, about 6 to about 19, about 7 to about 18, about 8 to about 17, about 9 to about 16, about 10 to about 15, or about 11 to about 14 consecutive amino acid sequence reactive center loop (RCL) portion of alpha-1 antirypsin (AAT) that is responsible for binding to and inactivating neutrophil elastase and that includes the Met358-Ser359 bond or a retro-inverso amino acid sequence of the amino acid sequence thereof. In some embodiments, the binding of the neutrophil elastase binding peptides or nanoparticles and/or microparticles coupled thereto can be sustained, as opposed to short-lived, to provide sustained binding of the neutrophil elastase binding peptides or nanoparticles and/or microparticles coupled thereto to the NE and neutrophils.

In some embodiments, the neutrophil elastase binding peptide can include an amino acid sequence that is at least about 60%, at least about 70%, at least about 80%, or at least about 90% identical to the amino acid sequence of EAIPMSIPPEVK (SEQ ID NO: 1) or a retro-inverso amino acid sequence of SEQ ID NO: 1. For example, the neutrophil elastase binding peptide can include a substitution of an amino acid of at least one of residue 4P, 5M, or 6S of EAIPMSIPPEVK (SEQ ID NO: 1).

In other embodiments, the neutrophil elastase binding peptide can include an amino acid sequence of $EAIX_1X_2X_3IPPEVK$ (SEQ ID NO: 2) or a retro-inverso amino acid sequence of SEQ ID NO: 2, wherein $X_1$ is P, A, S, N, or L, $X_2$ is A, C, D, E, F, G, H, I, K, L, M, N, P, Q, R, S, T, W, or Y, and $X_3$ is S or A.

In some embodiments, $X_2$ is M, if at least one of $X_1$ or $X_3$ is not S.

In other embodiments, $X_1$ is not P if $X_2$ is M and $X_3$ is S.

In still other embodiments, $X_2$ is not M if $X_1$ is P and $X_3$ is S.

In other embodiments, $X_3$ is not S if $X_1$ is P and $X_2$ is M.

In some embodiments, the neutrophil elastase binding peptide can include an amino acid sequence selected from the group consisting of:

EAIPMAIPPEVKF, (SEQ ID NO: 3)

EAIPVSIPPEVKF, (SEQ ID NO: 4)

-continued

EAIPASIPPEVKF, (SEQ ID NO: 5)

EAIPCSIPPEVKF, (SEQ ID NO: 6)

EAIPDSIPPEVKF, (SEQ ID NO: 7)

EAIPESIPPEVKF, (SEQ ID NO: 8)

EAIPFSIPPEVKF, (SEQ ID NO: 9)

EAIPGSIPPEVKF, (SEQ ID NO: 10)

EAIPHSIPPEVKF, (SEQ ID NO: 11)

EAIPISIPPEVKF, (SEQ ID NO: 12)

EAIPKSIPPEVKF, (SEQ ID NO: 13)

EAIPLSIPPEVKF, (SEQ ID NO: 14)

EAIPNSIPPEVKF, (SEQ ID NO: 15)

EAIPPSIPPEVKF, (SEQ ID NO: 16)

EAIPQSIPPEVKF, (SEQ ID NO: 17)

EAIPRSIPPEVKF, (SEQ ID NO: 18)

EAIPSSIPPEVKF, (SEQ ID NO: 19)

EAIPTSIPPEVKF, (SEQ ID NO: 20)

EAIPWSIPPEVKF, (SEQ ID NO: 21)

EAIPYSIPPEVKF, (SEQ ID NO: 22)

EAIAMSIPPEVKF, (SEQ ID NO: 23)

EAISMSIPPEVKF, (SEQ ID NO: 24)

EAINMSIPPEVKF, (SEQ ID NO: 25)

EAILMSIPPEVKF, (SEQ ID NO: 26)

EAIAMAIPPEVKF, (SEQ ID NO: 27)

EAISMAIPPEVKF, (SEQ ID NO: 28)

EAINMAIPPEVKF, (SEQ ID NO: 29)

EAILMAIPPEVKF, (SEQ ID NO: 30)

EAIPMAIPPEVK, (SEQ ID NO: 31)

-continued (SEQ ID NO: 32)
EAIPVSIPPEVK, (SEQ ID NO: 33)
EAIPASIPPEVK, (SEQ ID NO: 34)
EAIPCSIPPEVK, (SEQ ID NO: 35)
EAIPDSIPPEVK, (SEQ ID NO: 36)
EAIPESIPPEVK, (SEQ ID NO: 37)
EAIPFSIPPEVK, (SEQ ID NO: 38)
EAIPGSIPPEVK, (SEQ ID NO: 39)
EAIPHSIPPEVK, (SEQ ID NO: 40)
EAIPISIPPEVK, (SEQ ID NO: 41)
EAIPKSIPPEVK, (SEQ ID NO: 42)
EAIPLSIPPEVK, (SEQ ID NO: 43)
EAIPNSIPPEVK, (SEQ ID NO: 44)
EAIPPSIPPEVK, (SEQ ID NO: 45)
EAIPQSIPPEVK, (SEQ ID NO: 46)
EAIPRSIPPEVK, (SEQ ID NO: 47)
EAIPSSIPPEVK, (SEQ ID NO: 48)
EAIPTSIPPEVK, (SEQ ID NO: 49)
EAIPWSIPPEVK, (SEQ ID NO: 50)
EAIPYSIPPEVK, (SEQ ID NO: 51)
EAIAMSIPPEVK, (SEQ ID NO: 52)
EAISMSIPPEVK, (SEQ ID NO: 53)
EAINMSIPPEVK, (SEQ ID NO: 54)
EAILMSIPPEVK, (SEQ ID NO: 55)
EAIAMAIPPEVK, (SEQ ID NO: 56)
EAISMAIPPEVK, (SEQ ID NO: 57)
EAINMAIPPEVK, (SEQ ID NO: 58))
EAILMAIPPEVK, and retro-inverso amino acid sequences of SEQ ID Nos: 1-58.

The neutrophil elastase binding peptides can be subject to various changes, substitutions, insertions, and deletions where such changes provide for certain advantages in its use. In this regard, neutrophil elastase binding peptides that bind to and/or complex with a neutrophil elastase can be substantially homologous with, rather than be identical to, the sequence of a recited peptide where one or more changes are made and it retains the ability to function as specifically binding to and/or complexing with neutrophil elastase.

The neutrophil elastase binding peptides can be in any of a variety of forms of polypeptide derivatives, that include amides, conjugates with proteins, cyclized polypeptides, polymerized polypeptides, retro-inverso peptides, analogs, fragments, chemically modified polypeptides, and the like derivatives.

Retro-inverso peptides are linear peptides whose amino acid sequence is reversed and the α-center chirality of the amino acid subunits is inverted as well. These types of peptides are designed by including D-amino acids in the reverse sequence to help maintain side chain topology similar to that of the original L-amino acid peptide and make them more resistant to proteolytic degradation. D-amino acids represent conformational mirror images of natural L-amino acids occurring in natural proteins present in biological systems. Peptides that contain D-amino acids have advantages over peptides that just contain L-amino acids. In general, these types of peptides are less susceptible to proteolytic degradation and have a longer effective time when used as pharmaceuticals. Furthermore, the insertion of D-amino acids in selected sequence regions as sequence blocks containing only D-amino acids or in-between L-amino acids allows the design of peptide based drugs that are bioactive and possess increased bioavailability in addition to being resistant to proteolysis. Furthermore, if properly designed, retro-inverso peptides can have binding characteristics similar to L-peptides.

The term "analog" includes any polypeptide having an amino acid residue sequence substantially identical to a sequence specifically shown herein in which one or more residues have been conservatively substituted with a functionally similar residue and that specifically binds to and/or complexes with the neutrophil elastase as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and arylamines (e.g., triethylamine, diisopropylamine, methylamine, dimethylamine, and the like) and optionally substituted ethanolamines (e.g., ethanolamine, diethanolamine and the like).

The neutrophil elastase binding peptides can be synthesized by any of the techniques that are known to those skilled in the peptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

In some embodiments, the neutrophil elastase binding peptides described herein can be directly linked to at least one of a detectable moiety, therapeutic agent, theranostic agent, solid matrix, or carrier. In alternative embodiments, the neutrophil elastase binding peptides can be linked to at least one of a detectable moiety, therapeutic agent, theranostic agent, solid matrix, or carrier via a linking molecule.

For example, additional residues may also be added at either terminus of a neutrophil elastase binding peptide for the purpose of providing a "linker" by which the neutrophil elastase binding peptides can be conveniently linked and/or affixed to other detectable moieties, therapeutic agents, theranostic agents, polypeptides, proteins, labels, solid matrices, or carriers.

In addition, a subject neutrophil elastase binding peptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half-life of the peptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linking molecule is selected in part based on its ability to alter the phobicity (e.g., to cause the linked compound to become more hydrophilic or hydrophobic) depending on its desired use.

In some embodiments, the linker can be an amino acid linker or peptide linker that links the targeting peptide to other polypeptides, proteins, and/or molecules, such as detectable moieties, labels, therapeutic agents, theranostic agents, solid matrices, or carriers. A flexible peptide linker can be about 20 or fewer amino acids in length. For example, a peptide linker can contain about 12 or fewer amino acid residues, e.g., 1, 2, 3, 4, 5, 6, 7, 8, 9, 10, 11, and 12. In some cases, a peptide linker comprises two or more of the following amino acids: glycine, serine, lysine, alanine, and threonine. Where the linker is a peptide linker, the polypeptide-linker may be produced as a single recombinant polypeptide using a conventional molecular biological/recombinant DNA method.

For example, the neutrophil elastase binding peptide can include lysines that can be capable of reacting with a carbonyl-containing group, such as an anhydride or an acid halide, or with an alkyl group containing a good leaving group (e.g., a halide). The neutrophil elastase binding peptide can also include cysteines that facilitate chemical coupling via thiol-selective chemistry (e.g., maleimide-activated compounds). Further, the neutrophil elastase binding peptides can include tyrosines, which can be modified using diazonium coupling reactions. In an exemplary embodiment, the amino acid residue linker is a cysteine-glycine (CG) linker. For example, the linker can include CG residues linked to the 1E residue of the amino acid sequence of EAIPMSIPPEVK (SEQ ID NO: 1) or EAIPMSIPPEVKF (SEQ ID NO: 59).

In other embodiments, a chemical binder group can be used. A binder group can serve to increase the chemical reactivity of a substituent on either the neutrophil elastase binding peptide or the compound or molecule to which the neutrophil elastase binding peptide is bound, and thus increase the coupling efficiency. Binder chemistries can include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation.

Useful functional groups are present on the neutrophil elastase binding peptides based on the particular amino acids present, and additional groups can be designed. It will be evident to those skilled in the art that a variety of bifunctional or polyfunctional reagents, both homo- and heterofunctional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to peptides are described by U.S. Pat. No. 7,666,624.

In other embodiments, the neutrophil elastase binding peptides can be tethered to compounds or molecules, such as detectable moieties, labels, therapeutic agents, theranostic agents, solid matrices, or carriers, via a polymer tether. The polymer tether can be linked to the compounds or molecules directly or indirectly by any means. For example, the polymer tether can be linked to the compounds or molecules using a covalent link, a non-covalent link, an ionic link, and a chelated link, as well as being absorbed or adsorbed onto the compounds or molecules. In addition, the polymer tether can be linked to the compounds or molecules through hydrophobic interactions, hydrophilic interactions, charge-charge interactions, π-stacking interactions, combinations thereof, and like interactions.

In some embodiments, the targeting peptides can be conjugated to compound or molecules, such as detectable moieties, labels, therapeutic agents, theranostic agents, solid matrices, or carriers, via a PEG molecule linker. The PEG molecules can have a variety of lengths and molecular weights, including, for example, PEG 200, PEG 1000, PEG 1500, PEG 4600, PEG 10,000, or combinations thereof.

In some embodiments, a plurality of neutrophil elastase binding peptides described herein can be linked to or bound to a biocompatible, biodegradable nanoparticle and/or microparticle core construct. By way of example, FIG. 1 schematically illustrates a nanoparticle construct 10 that includes a plurality of neutrophil elastase binding peptides 12 bound to a nanoparticle core 14. The plurality of neutrophil elastase binding peptides 12 can be bound to, conjugated to, and/or decorated on the surface defined by the nanoparticle core 14. The neutrophil elastase binding peptides can be spatially or topographically arranged on the nanoparticle surface such that the neutrophil elastase binding peptides 12 do not spatially mask each other and the nanoparticle is able to bind to an activated neutrophil with exposed neutrophil elastase, thereby enhancing retention of the nanoparticle construct 10 onto activated neutrophils.

The nanoparticles and/or microparticles can be made from any biocompatible, biodegradable material that can form a nanoparticle or microparticle to which the activated neutrophil or neutrophil elastase binding peptides described herein can be attached, conjugated, and/or decorated. Examples of nanoparticles and/or microparticles can include liposomes, lipidic nanoparticles, a hydrogel microparticles or nanoparticles, micelles, metal nanoparticles, polymer nanoparticles, dendrimers, quantum dots, and/or combinations of these materials. The nanoparticles and/or microparticles can include and/or be surface modified or engineered with the activated neutrophil or neutrophil elastase binding peptides. In some embodiments, the nanoparticles or microparticles can be optically or magnetically detectable. In other embodiments, intrinsically fluorescent or luminescent nanoparticles or microparticles, nanoparticles and/or microparticles that comprise fluorescent or luminescent moieties, plasmon resonant nanoparticles, and magnetic nanoparticles are among the detectable nanoparticles that can be used.

The nanoparticles and/or microparticles can have a maximum length or diameter of about 100 nm to about 10 μm. In general, the nanoparticle or microparticle construct can have dimensions small enough to allow a composition comprising the nanoparticle or microparticle constructs to be systemically administered to a subject and targeted to activated neutrophils and tissue of the subject. In some embodiments, the nanoparticle or microparticle construct can have a size that facilitates encapsulation of one or more therapeutic and/or imaging agents.

The nanoparticles and/or microparticles of the composition may be uniform (e.g., being about the same size) or of variable size. Particles may be any shape (e.g., spherical or rod shaped), but are preferably made of regularly shaped material (e.g., spherical). Other geometries can include substantially spherical, circular, triangle, quasi-triangle, square, rectangular, hexagonal, oval, elliptical, rectangular with semi-circles or triangles and the like. Selection of suitable materials and geometries are known in the art.

In other embodiments, the nanoparticles and/or microparticles can include lipidic nanoparticles or microparticles, polymer nanoparticles and/or microparticles, liposomes, and/or dendrimers with a membrane, shell, or surface that is formed from a naturally-occurring, synthetic or semi-synthetic (i.e., modified natural) material. In some embodiments, the lipidic nanoparticles or liposomes can include a membrane or shell that is formed from a naturally-occurring, synthetic or semi-synthetic material that is generally amphipathic (i.e., including a hydrophilic component and a hydrophobic component). Examples of materials that can be used to form the membrane or shell of the lipidic nanoparticle or microparticle or liposome include lipids, such as fatty acids, neutral fats, phospholipids, oils, glycolipids, surfactants, aliphatic alcohols, waxes, terpenes, and steroids. Semi-synthetic or modified natural lipids can include natural lipids that have been chemically modified in some fashion. The lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethylammonium chloride, and common natural lipids derivatized to contain one or more basic functional groups.

Other examples of lipids, any one or combination of which may be used to form the membrane or shell of the lipidic nano-particle or liposome, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, DE), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl) carbonyl)methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

Examples of biocompatible, biodegradable polymers that can be used to form the nanoparticles are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide) s, biodegradable polyurethanes, and blends and/or copolymers thereof.

Other examples of materials that may be used to form the nanoparticles and/or microparticles can include chitosan, poly(ethylene oxide), poly(lactic acid), poly(acrylic acid), poly(vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly (glycolide), poly(lactide-co-glycolide), poly(amide), poly (hydroxylacid), poly(sulfone), poly(amine), poly (saccharide), poly(HEMA), poly(anhydride), gelatin, glycosaminoglycans (GAG), poly(hyaluronic acid), poly (sodium alginate), alginate, albumin, hyaluronan, agarose, polyhydroxybutyrate (PHB), copolymers thereof, and blends thereof.

In some embodiments, the nanoparticle and/or microparticle can include a liposome. The liposome can be an unilamellar liposome. The liposome can have a width less than about 200 nm. For example, the width of the liposome can be about 100 nm to about 150 nm. In some embodiments, the liposome is about 150 nm in diameter. The liposome can have a high cholesterol content (e.g., about 40%) in the membrane in order to efficiently encapsulate a water-soluble thrombolytic drug protecting the drug from plasma deactivation in circulation and prevent premature drug leakage due to membrane rigidity.

In some embodiments, liposome nanoparticles having a diameter of 150 nm can be prepared by homogenizing DSPC (49 mol %), and DSPE-PEG-peptide (5 mol %), cholesterol (45 mol %) in 1:1 chloroform:methanol and subjecting the mixture to reverse phase evaporation through several cycles of freeze-thaw, followed by extrusion through a 200 nm polycarbonate membrane to achieve unilamellar vesicles. The particles can then be surface-modified with the neutrophil elastase binding peptides at a surface density effective to promote maximum particle adhesion to exposed activated neutrophil surfaces and retention at low-to-high sheer stresses.

In other embodiments, the nanoparticles can include quantum dots, i.e., bright, fluorescent nanocrystals with physical dimensions small enough such that the effect of quantum confinement gives rise to unique optical and electronic properties. In certain embodiments, the nanoparticles are optically detectable nanoparticles, such as metal nanoparticles. Metals used to form the nanoparticles include, but not limited to, Ag, Au, Cu, Al, Fe, Co, Ni, Ru, Rh, Pd, and Pt or oxides thereof. In another embodiment, the metal comprises Fe or iron oxide. A further surface functional layer can be added or formed in combination with a metal core material. Such functional layers can include, but are not limited to, Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, tin oxide, antimony oxide, iron oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylprorolidone (PVP), and other polymers; stacked multiple layers at least two layers including above listed metal layers and non-metal layers, and the like. In some embodiments, the metal core can be Au, Ag, Fe, Ti, Ni, Cr, Pt, Ru, NiCr alloy, NiCrN, PtRh alloy, CuAuCo alloy, IrRh alloy and/or WRe alloy. The metals used should be biocompatible.

In still other embodiments, the nanoparticle and/or microparticle can be a magnetic nanoparticle and/or microparticle. "Magnetic particles" refers to magnetically responsive particles that contain one or more metals or oxides or hydroxides thereof. Compositions including optically detectable metal nano-particles or quantum dots can be detected in vivo upon systemic administration to a subject using magnetic resonance imaging (MRI), magnetic resonance spectroscopy (MRS), nuclear magnetic resonance imaging (NMR), multimodal imaging, fluorescent, positron emission tomography (PET), near infrared (NIR) imaging, X-ray imaging, and computed tomography (CT).

In some embodiments, the nanoparticle and/or microparticle constructs can be decorated with other targeting agents or moieties besides the neutrophil elastase binding peptides described herein. The targeting agents can comprise any molecule, or complex of molecules, which is/are capable of interacting with a biomarker of, for example, a cell, cell fragment, or tissue, to which the nanoparticle and/or microparticle constructs are targeted. The biomarker can include, for example, a cellular protease, a kinase, a protein, a cell surface receptor, a lipid, and/or fatty acid. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments, carbohydrates), and small entities (e.g., small molecules, neurotransmitters, substrates, ligands, hormones, and elemental compounds). For example, the other targeting agents can include, for example, platelet targeting peptides, fibrin binding peptides, endothelium targeting agents, cancer cell targeting agents, and immune cell targeting peptides.

In some embodiments, the platelet targeting peptide can include a GPIIb-IIIa-binding peptide, such as a fibrinogen-mimicking peptide, GPIb binding peptide, such as a vWF-mimicking peptide, and/or a P-selectin glycoprotein ligand-1 specific for p-selectin. Natural ligands binding to these receptors are responsible for stabilizing active platelet interactions at vascular disease sites under a hemodynamic shear environment.

Such ligand molecules for use in a composition of the application include ligands that have been modified to increase their specificity of interaction with a target receptor, ligands that have been modified to interact with a desired receptor not naturally recognized by the ligand, and fragments of such ligands. Peptide ligands can also include small protein-like chains designed to mimic a peptide ligand (peptidomimetics). In some embodiments, the targeting moiety can include a small molecule peptide ligand. Preparation of peptide ligands can be accomplished by any number of methods for generating peptides.

Advantageously, peptide targeting moieties can each include about 5 to about 30 amino acids. By limiting the size of the peptides to about 5 to about 30 amino acids, the platelet targeting moieties can be spatially or topographically arranged on the nanoparticle or microparticle surface such that the neutrophil elastase binding peptides and platelet targeting moieties do not spatially mask each other and are able to adhere to an activated platelet surface with exposed surface receptors and enhance adhesion and retention of the nanoparticle or microparticle constructs to areas where activated neutrophils and activated platelets are present, such as areas of vascular injury.

Figure 2:
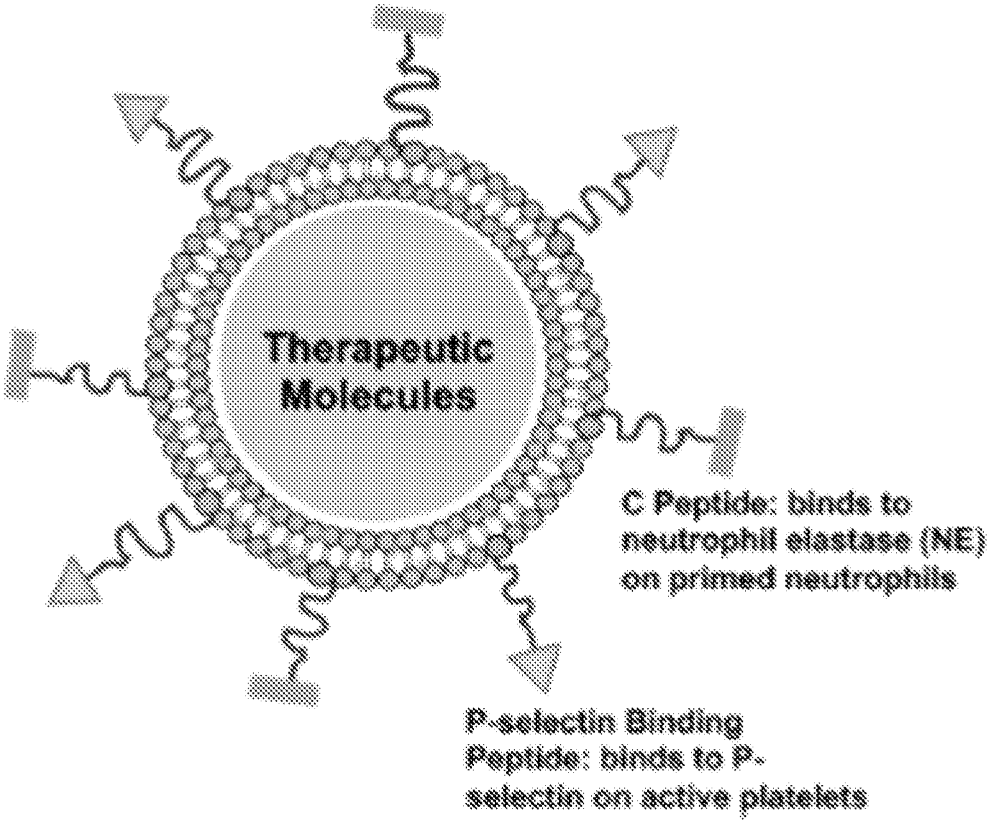
FIG. 2 is a schematic illustration showing the design of a liposomal construct surface-functionalized with neutrophil elastase binding peptides and P-selectin binding peptides.
Figure 3C:
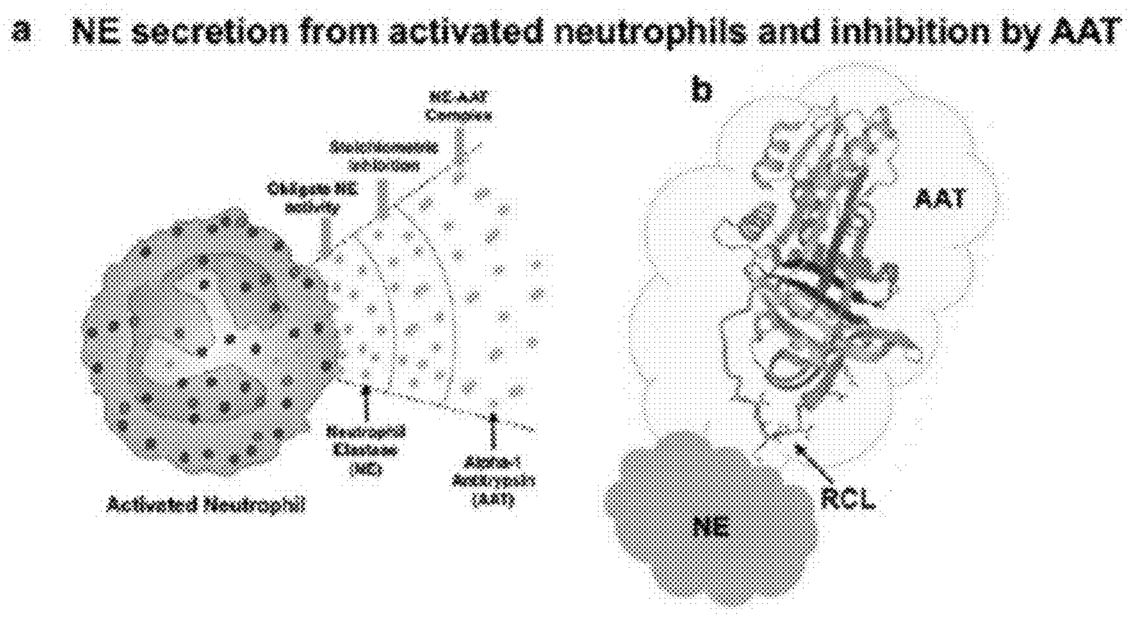
FIGS. 3(A-I) illustrate: (A) Neutrophil Elastase (NE) secretion from activated neutrophils and its stoichiometric inhibition by alpha-antitrypsin (AAT) radially distal from the neutrophil; (B) AAT binding to NE through reactive center loop (RCL); (C) Example of an RCL-derived NE binding peptide (NEBP); (D) HPLC-based analysis of NEBP interaction with mouse and human NE shows that such peptides are not cleaved by NE; (E) Surface Plasmon Resonance (SPR)-based analysis of NEBP binding to mouse NE (m-NE) shows high affinity binding; (F) Schematic of lipid conjugation to NEBP and to active platelet P-selectin binding peptide (PBP), and manufacture of nanoparticles with such lipopeptide systems to form neutrophil-targeted nanoparticle (NT-NP) and platelet-neutrophil-targeted nanoparticle (PNT-NP); (G) Dynamic Light Scattering (DLS) based size characterization of nanoparticles show diameter of ~150-200 nm; (H) SPR-based analysis of NT-NP binding to human NE. (I) (h-NE) shows high affinity of binding compared to untargeted nanoparticle (U-NP).
Figure 3C:
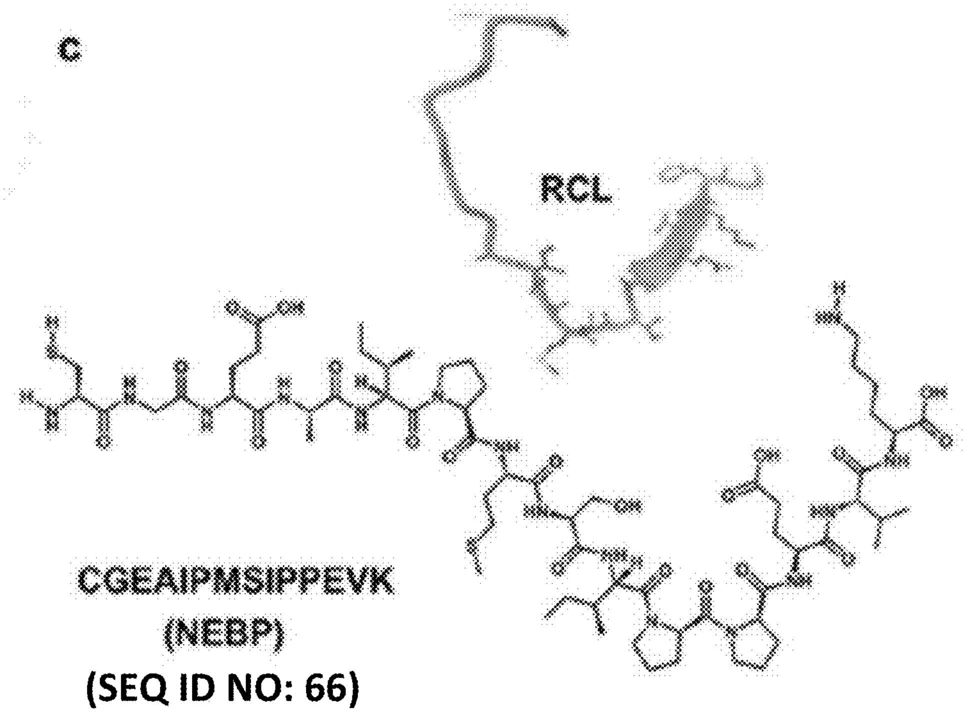
Figure 3D:
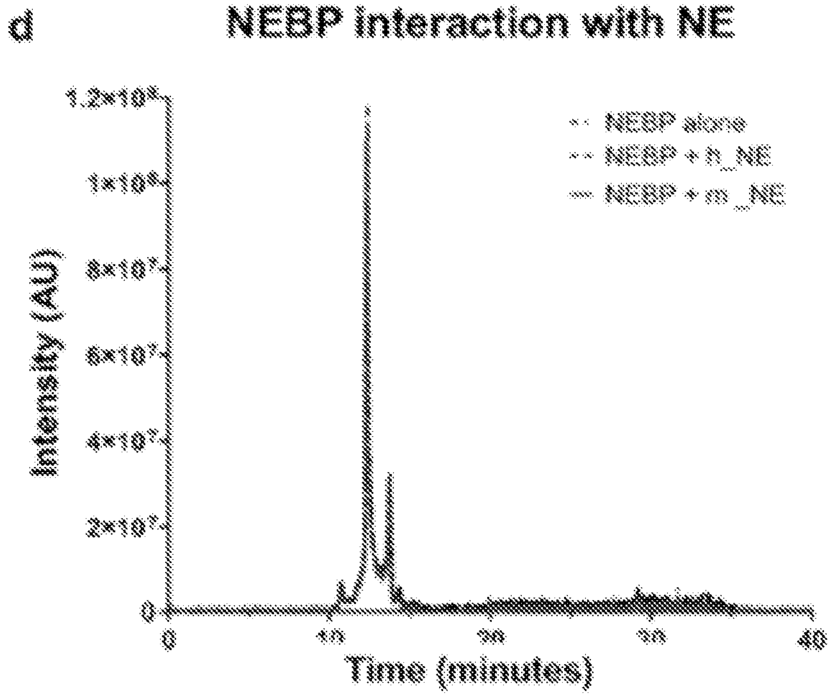
Figure 3E:
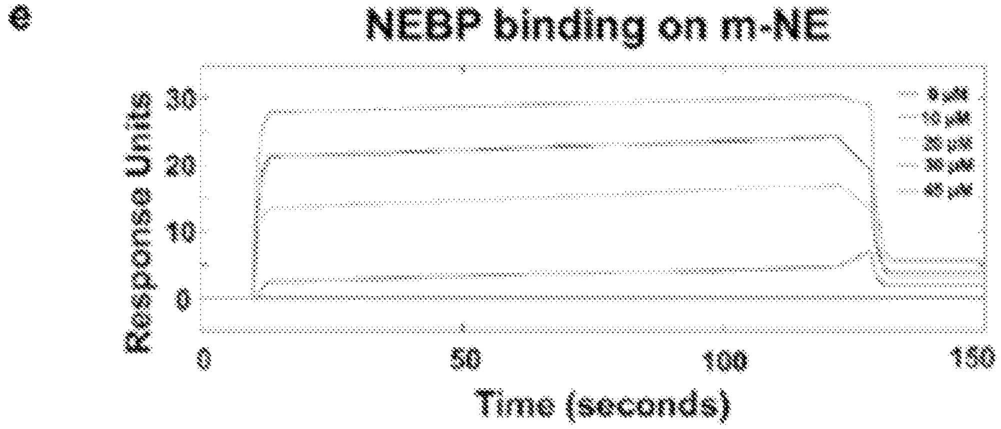
Figure 3F:
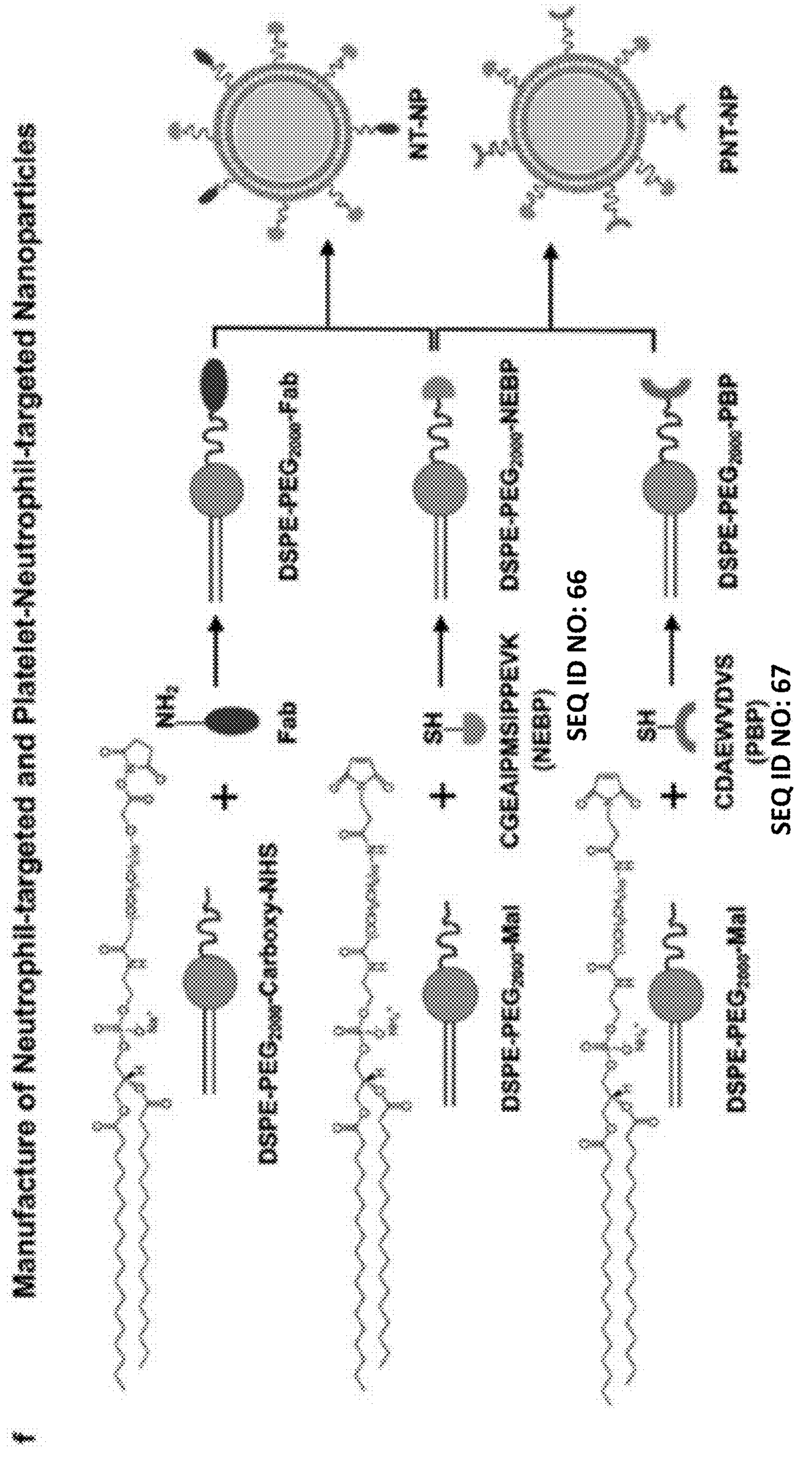
Figure 3G:
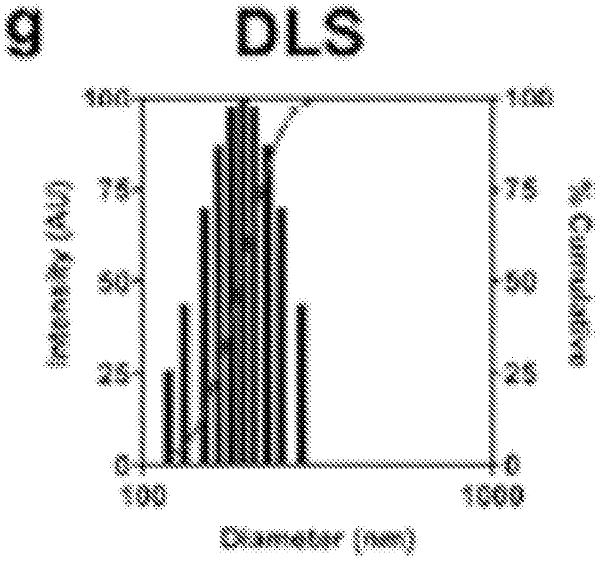
Figure 3H:
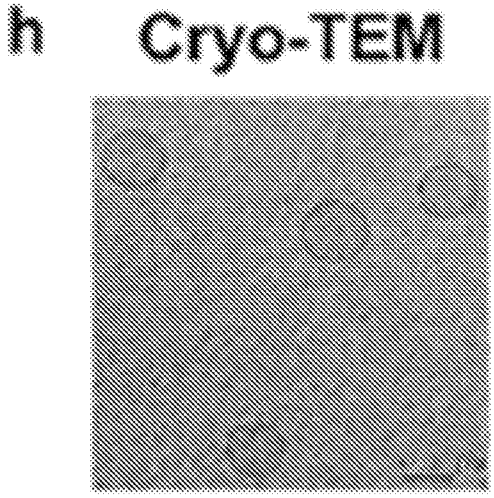
Figure 3I:
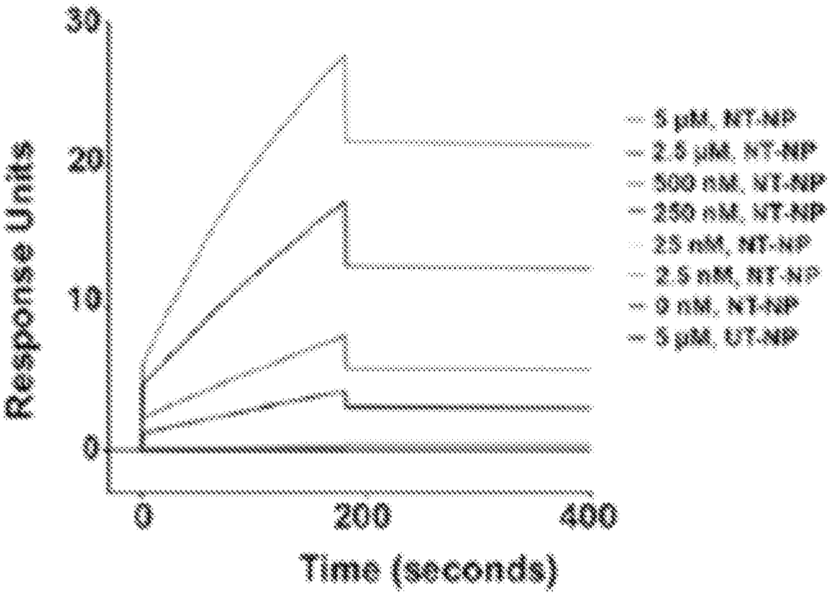
Figure 4A:
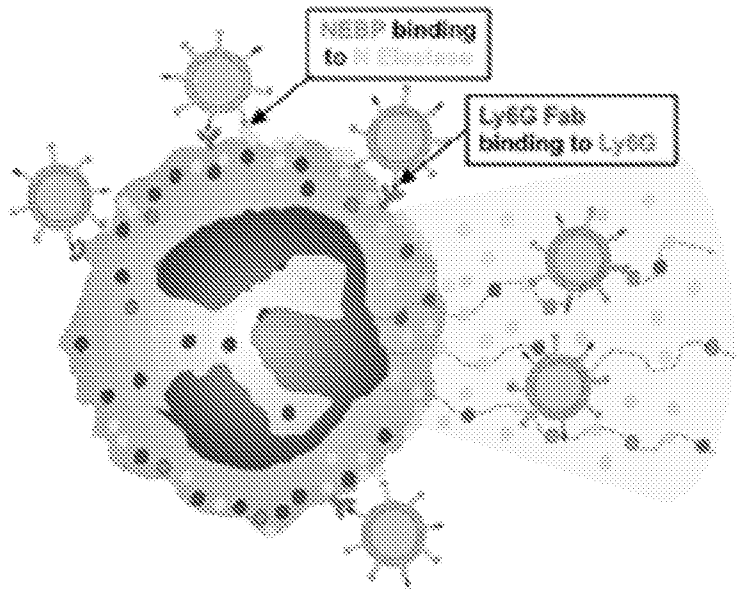
FIGS. 4(A-H) illustrate: (A) schematic of NT-NP binding to activated neutrophil; (B) NP effect on neutrophil viability shows that NT-NP is minimally toxic to neutrophils (similar to untargeted nanoparticle, U-NP); (C) Confocal fluorescence microscopy studies show that untargeted NP (U-NP) does not bind to inactive or activated fMLP-neutrophils, while NT-NP can specifically bind to fMLP-activated neutrophils (Blue: DAPI staining of neutrophil nucleus, Green: Neutrophil Elastase secreted from activated neutrophils, Red: Nanoparticles); (D) Flow cytometry analysis confirms enhanced binding of NT-NP to activated neutrophils (AN) compared to U-NP; (E) In vivo circulation time analysis by Rhodamine-B (RhB) fluorescence signal measurement in retro-orbitally drawn blood from mice injected with RhB-labeled U-NP and NT-NP show circulation half-life of NT-NP to be ~8 hrs; (F) In vivo studies in mice with LPS injection and neutrophil activation shows that NT-NP can bind to activated neutrophils in mouse retinal vasculature; (G) and (H): Quantitative analysis of NP co-localization with neutrophils in vivo confirms high co-localization of NT-NP with activated neutrophils, confirming specific targeting.
Figure 4B:
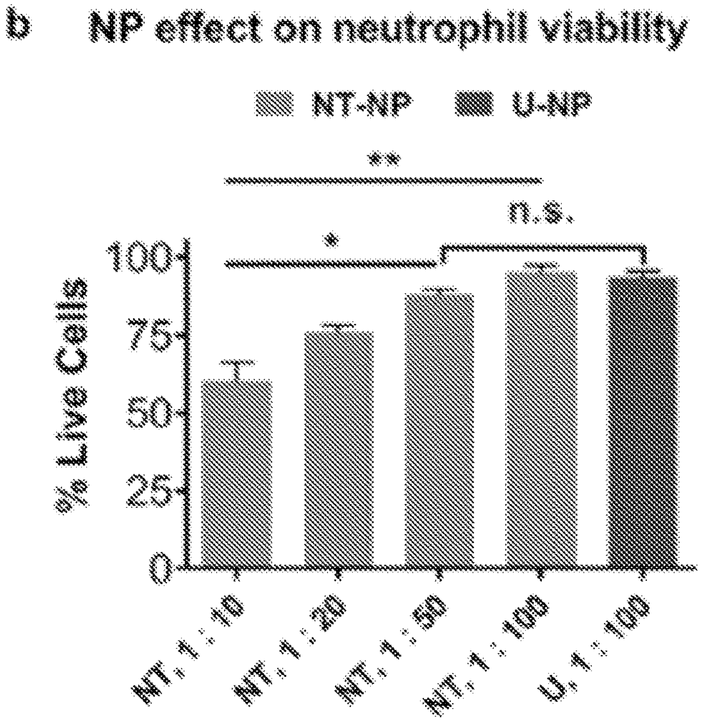
Figure 4C:
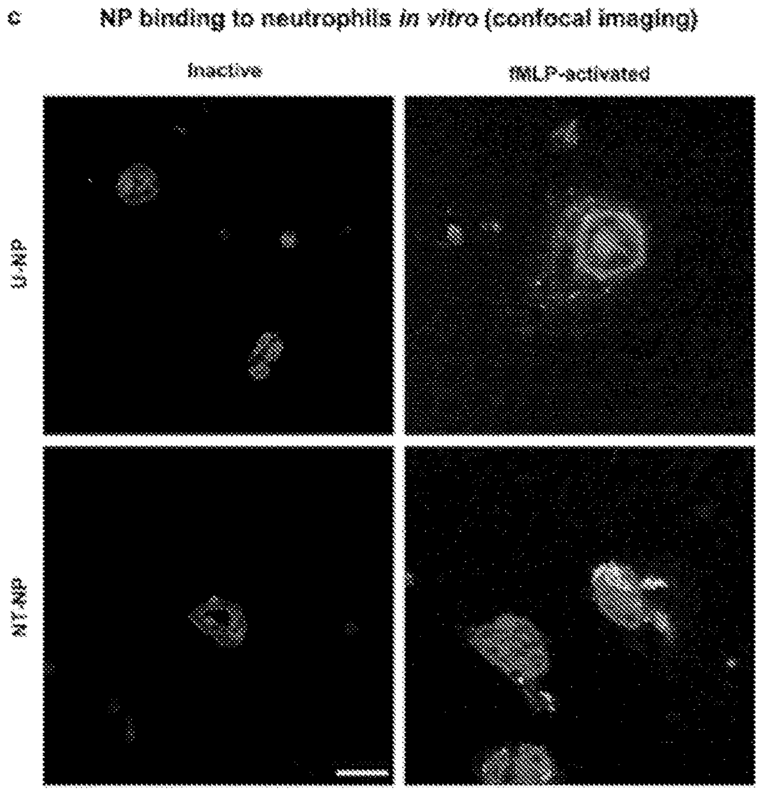
Figure 4D:
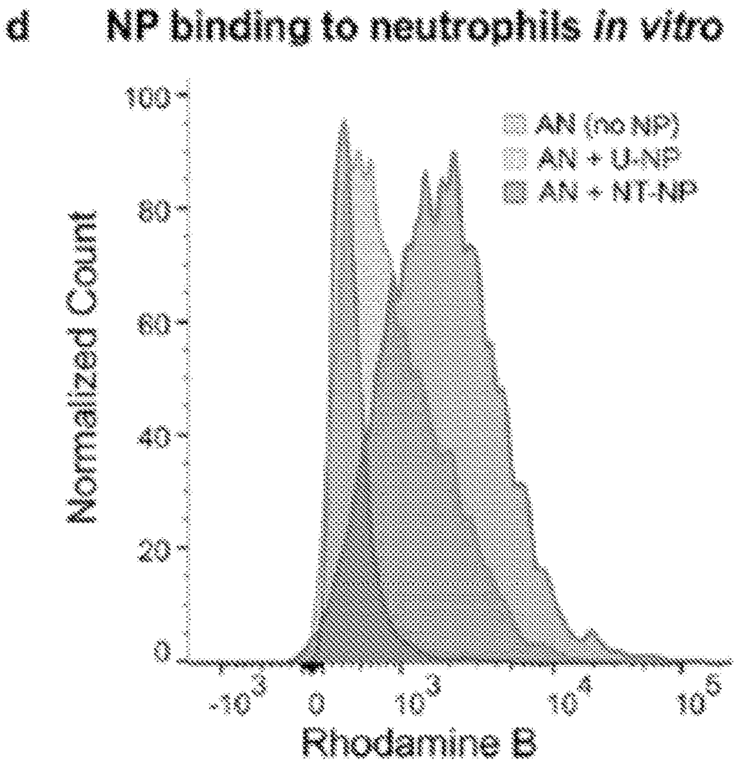
Figure 4E:
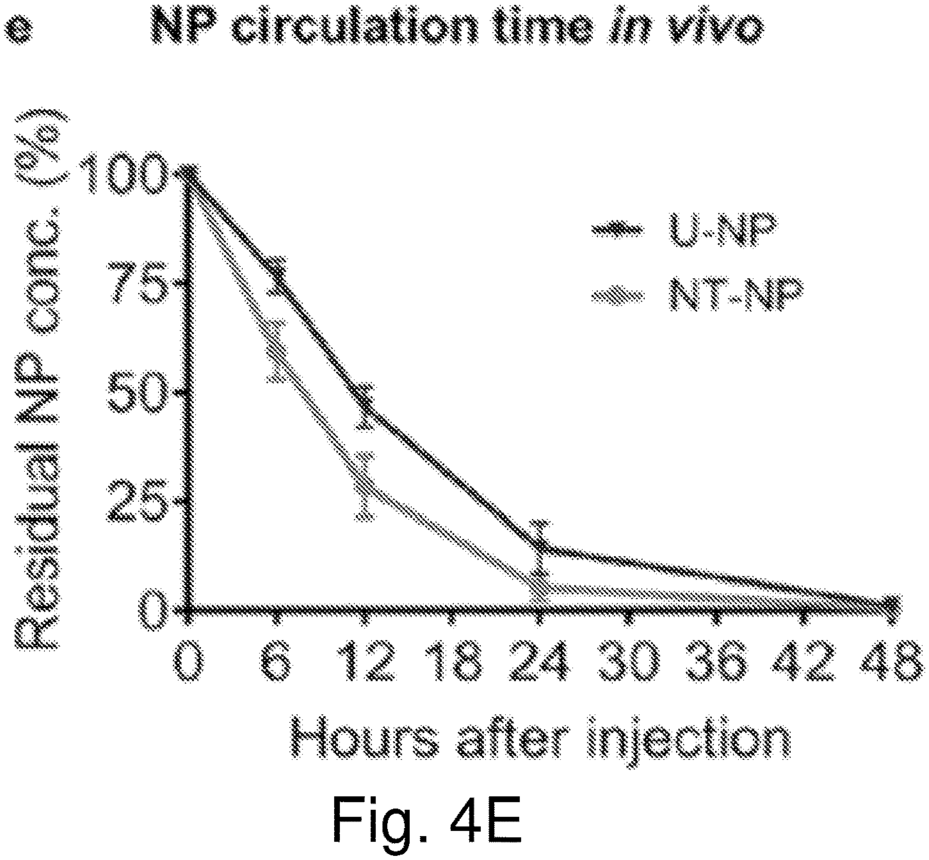
Figure 4F:
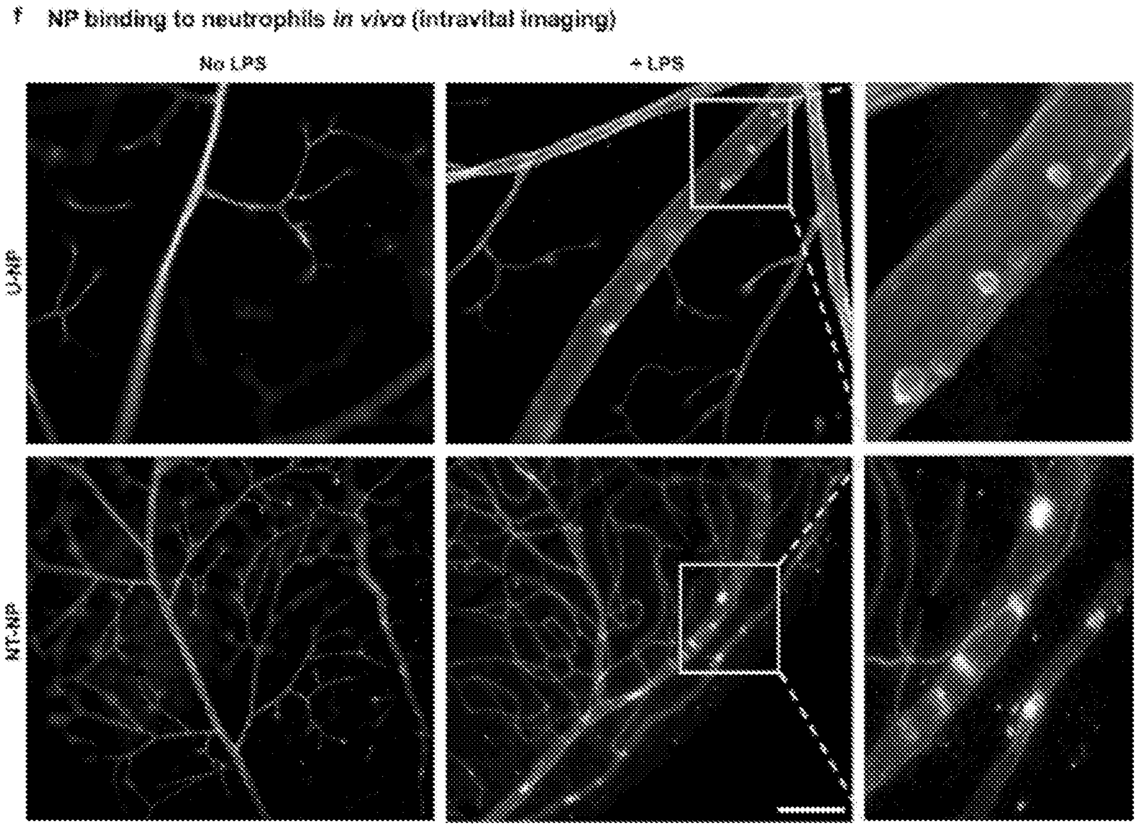
Figures 4G, 4H:
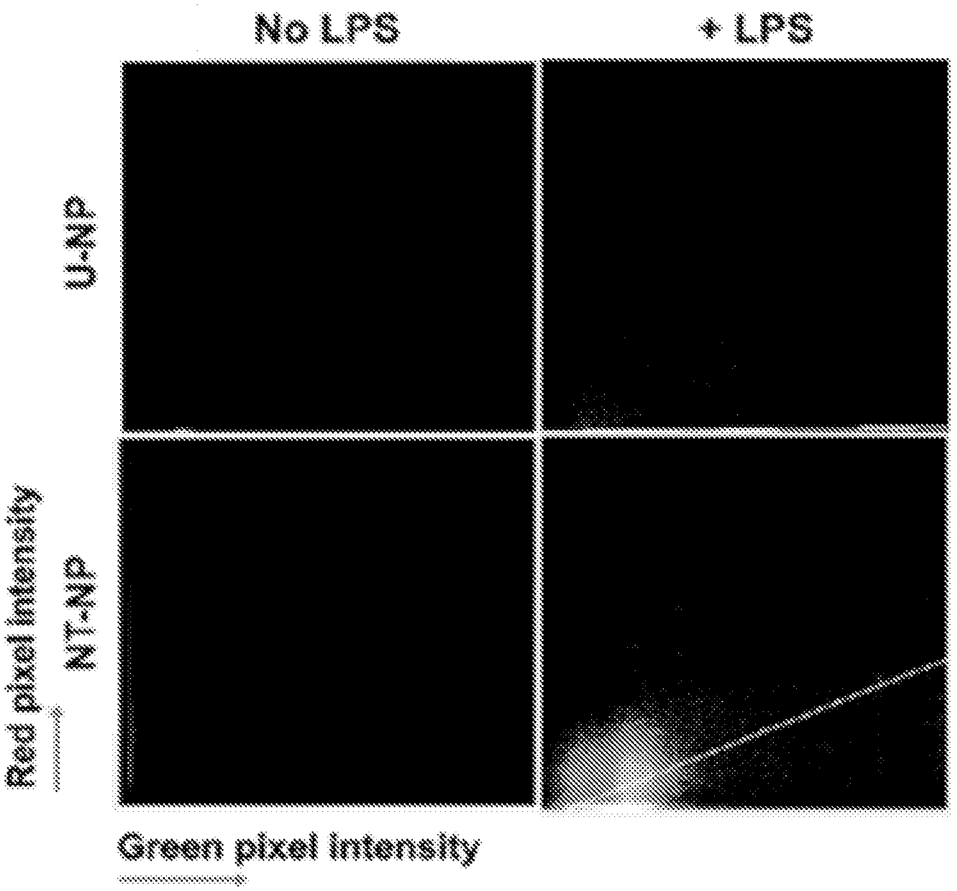
Figure 5A:
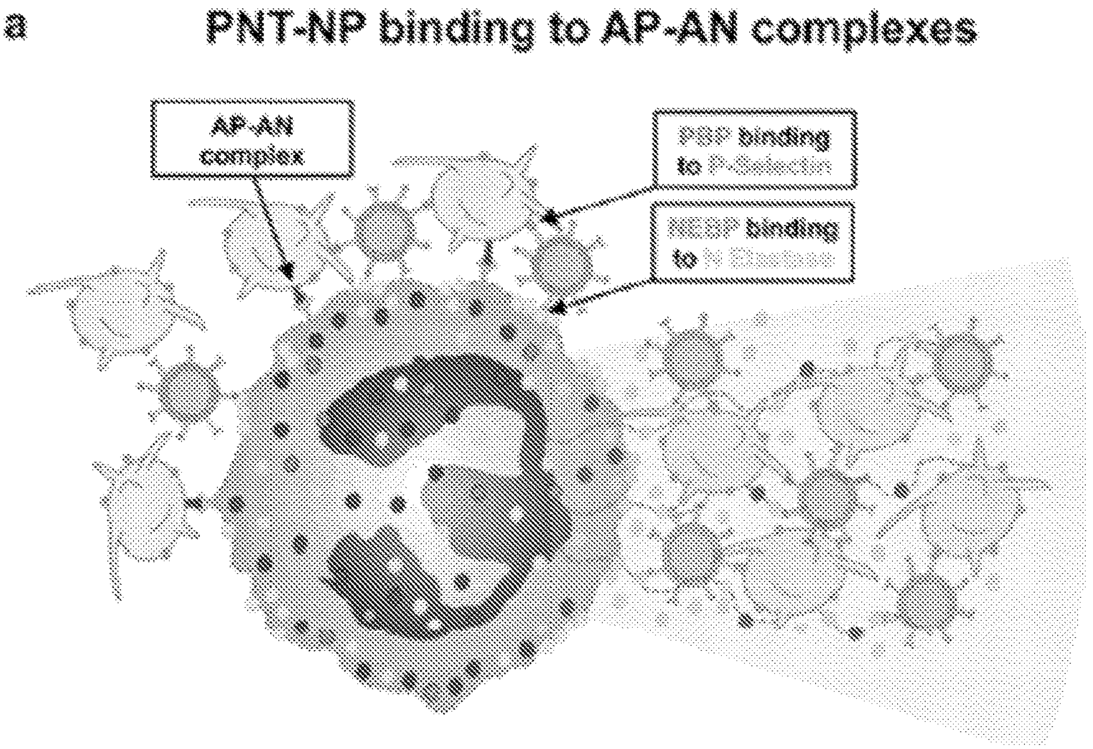
FIGS. 5(A-E) illustrate: (A) a schematic of PNT-NP binding to activated platelet-neutrophil (AP-AN complexes); (B) In vitro fluorescence-based studies with isolated neutrophils and platelets confirm that activated platelets and activated neutrophils form AP-AN complexes and PNT-NP can bind significantly more to these AP-AN complexes compared to untargeted nanoparticles (U-NP); (C) Quantitative fluorescence analysis from the above in vitro studies confirms significantly enhanced binding of PNT-NP to AP-AN complexes; (D) Flow cytometry analysis confirms that PNT-NP has significantly enhanced binding to activated neutrophils (AN) in AP-AN complexes; (E) Flow cytometry analysis confirms that PNT-NP has significantly enhanced binding to activated platelets (AP) in AP-AN complexes.
Figure 5C:
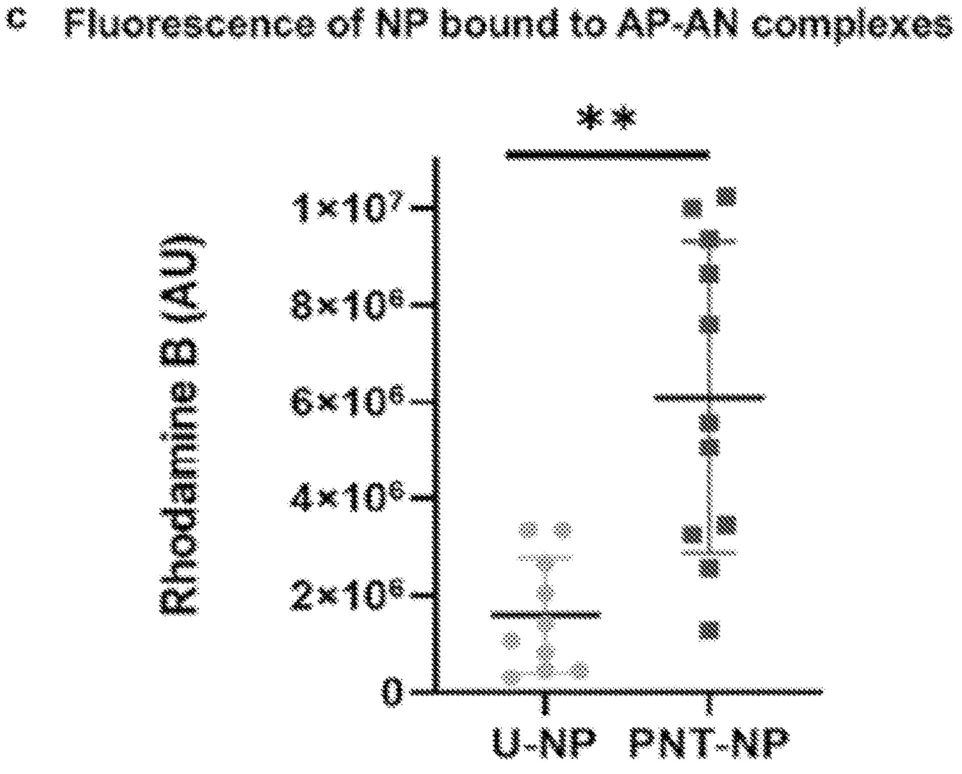
Figure 5B:
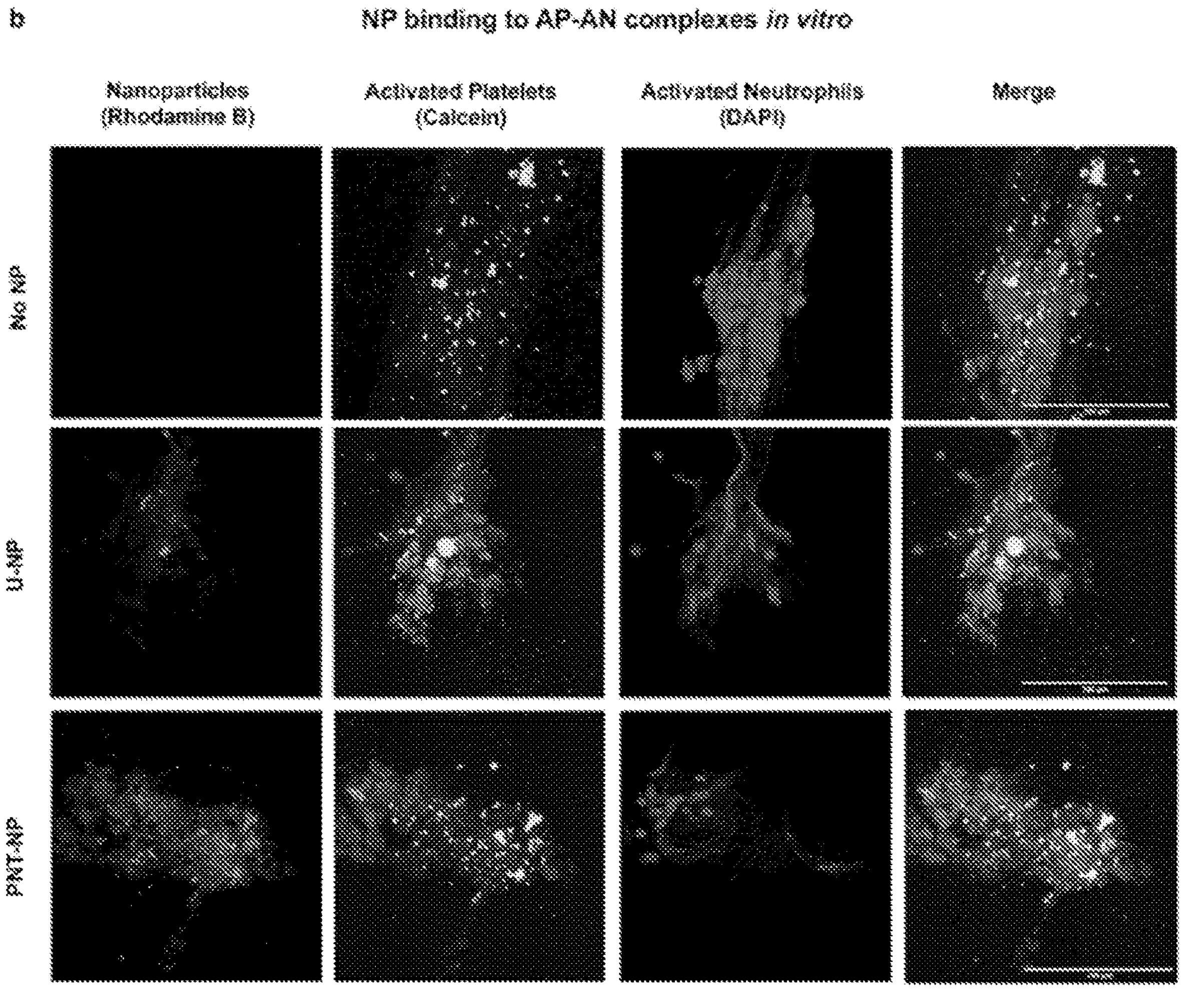
Figure 5D:
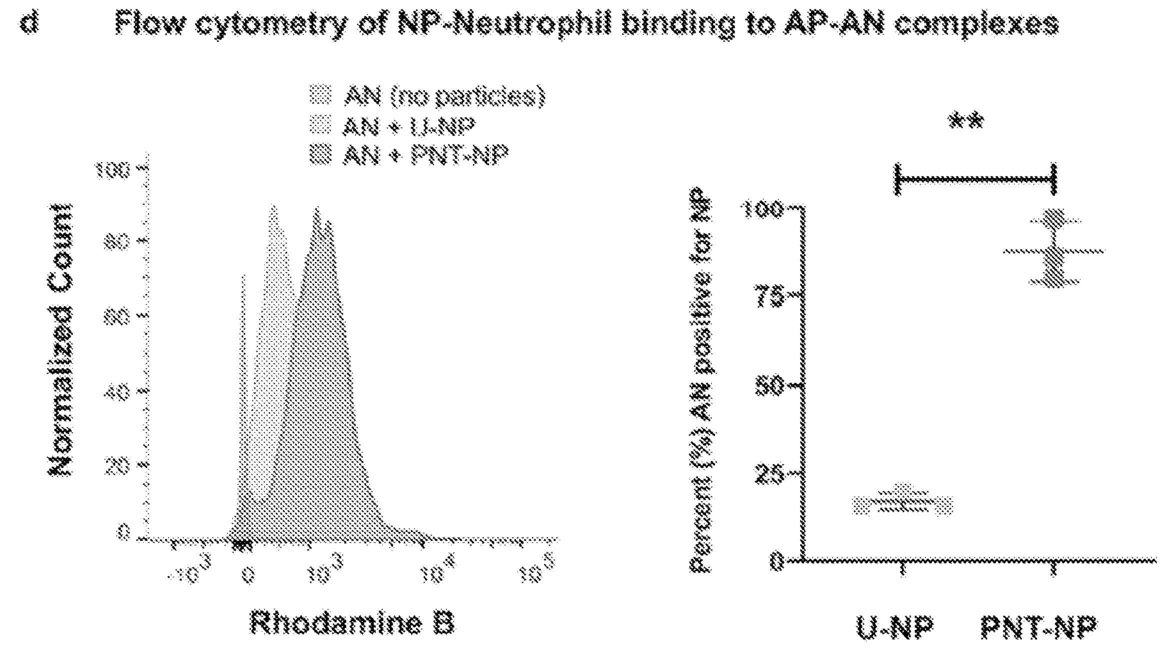
Figure 5E:
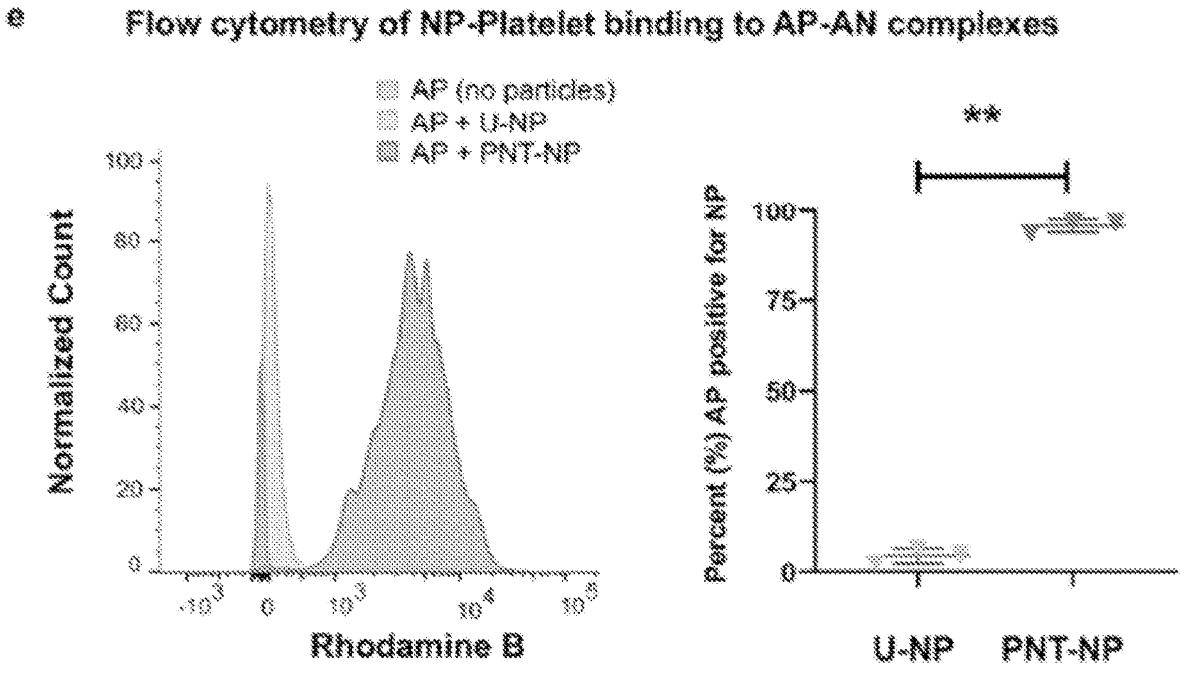
Figure 6A:
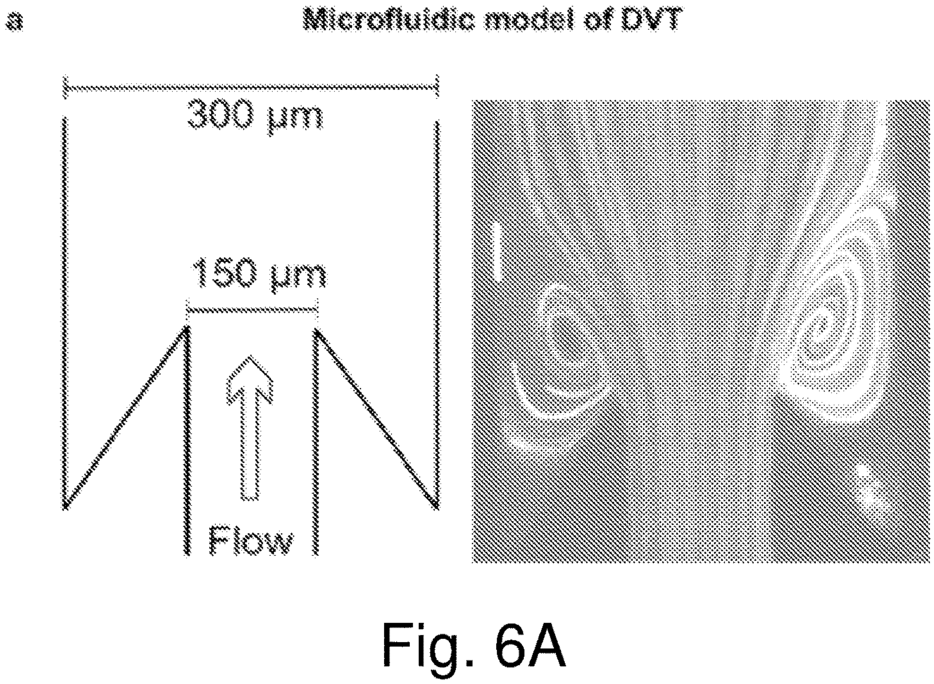
FIGS. 6(A-H) illustrate: (A) Schematic of microfluidic model of Deep Vein Thrombosis (DVT); (B) In vitro fluorescence-based studies under flow of human blood with fMLP-activated neutrophils and thrombin-activated platelets in the DVT microfluidic system shows enhanced binding of PNT-NP compared to U-NP to the thrombus forming in the 'valve pocket' of the microfluidic system (individual thrombus component fluorescence and NP fluorescence are labeled); (C) Using hydroxychloroquine (HCQ) as a model drug it is shown that 'free HCQ' affects neutrophil viability at and above $10^3$ ng/ml but when encapsulated within PNT-NP (HCQ-PNT-NP) the cell viability is maintained even at $10^7$ ng/ml, demonstrating that drug encapsulation within the PNT-NP enhances safety profile of the drug towards neutrophils; (D) HCQ_PNT-NP reduces neutrophil elastase (NE) activity from fMLP-activated neutrophils at levels similar to inhibition by AAT; (E) HCQ-PNT-NP reduces NETosis in fMLP-activated neutrophils reflected by the reduction in a characteristic NET marker, namely, citrullinated histone 3 (H3-C); (F) Intravenous administration of HCQ in mouse shows that administration of free HCQ results in high lethality while administration of HCQ-PNT-NP has minimum lethality, further signifying that drug encapsulation within PNT-NP improves drug safety profile in vivo; (G) Schematic of mouse inferior vena cava (IVC) ligation model of DVT; (H) Quantitative analysis as well as gross anatomical images of thrombi show that administration of HCQ_PNT-NP in mouse IVC DVT model reduces thrombus weight (and size), compared to HCQ_U-NP, signifying that targeted delivery of HCQ using PNT-NP as carrier platform results in significantly enhanced therapeutic effect.
Figure 6B:
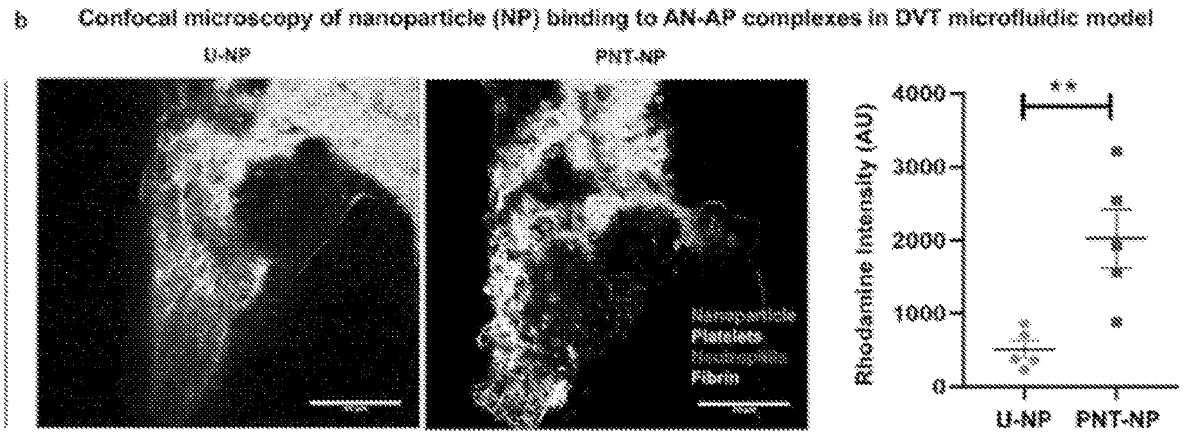
Figure 6C:
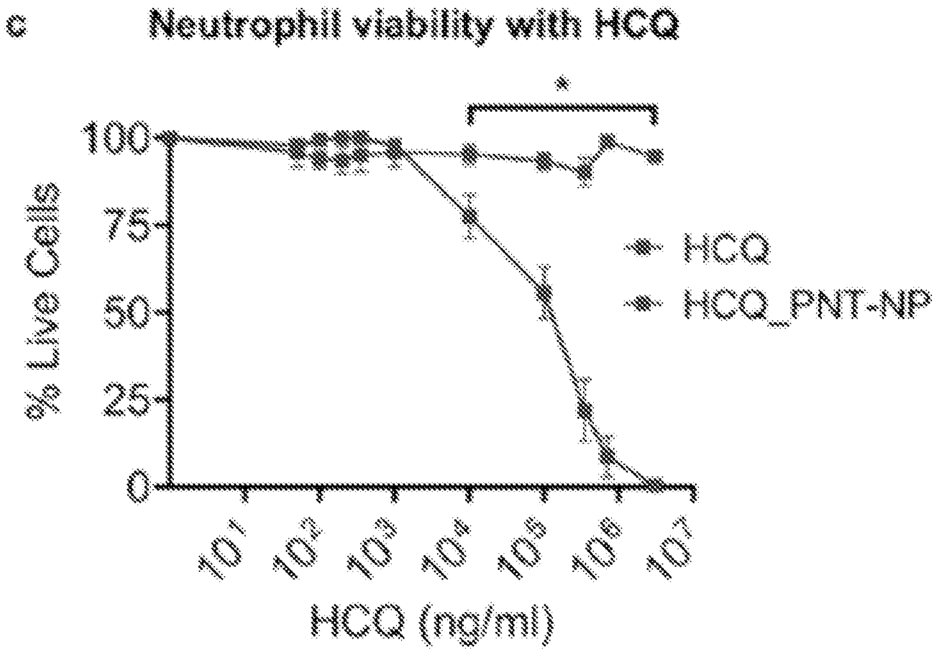
Figure 6D:
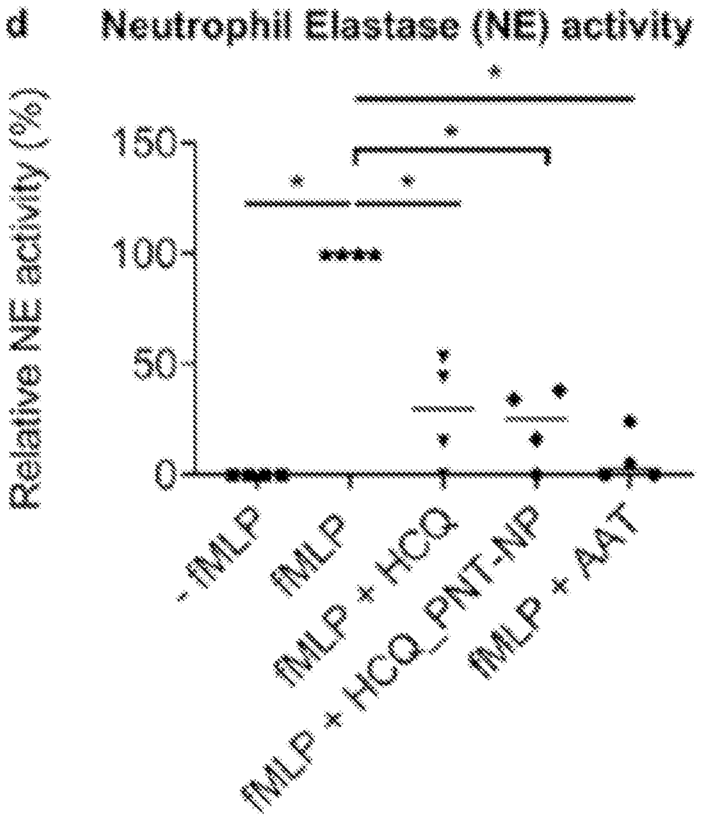
Figure 6E:
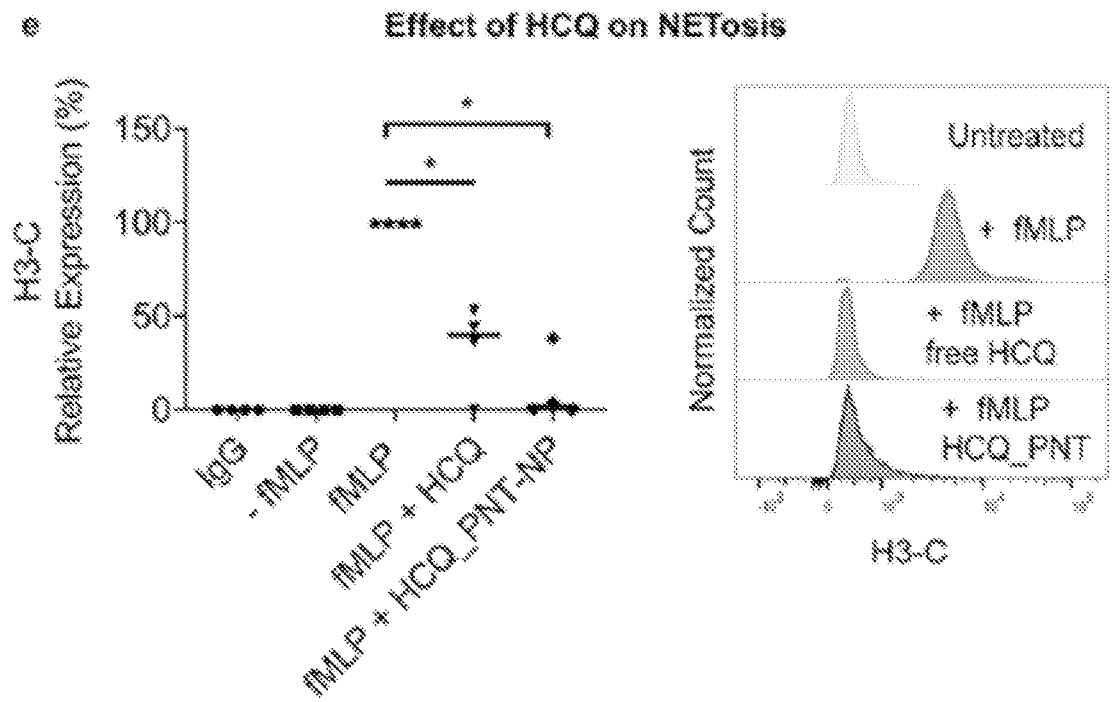
Figure 6F:
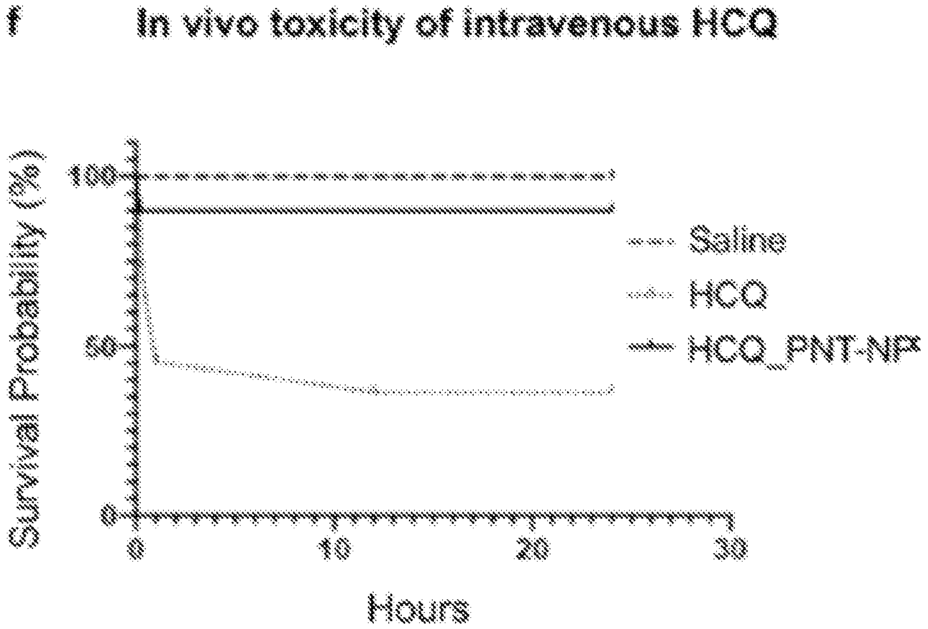
Figure 6G:
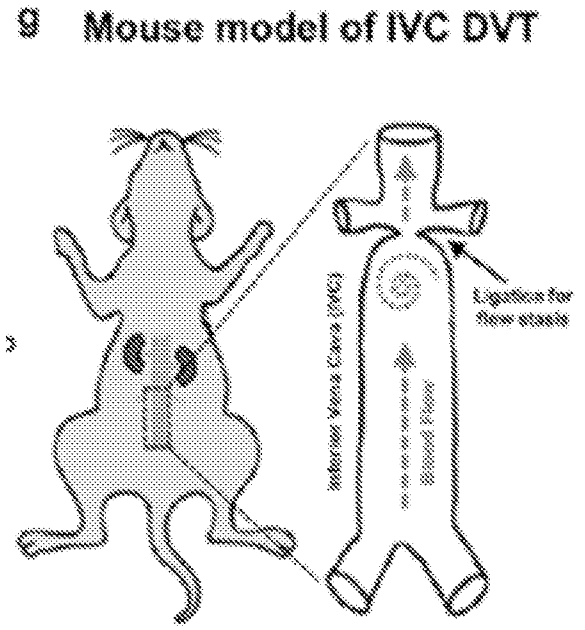
Figure 6H:
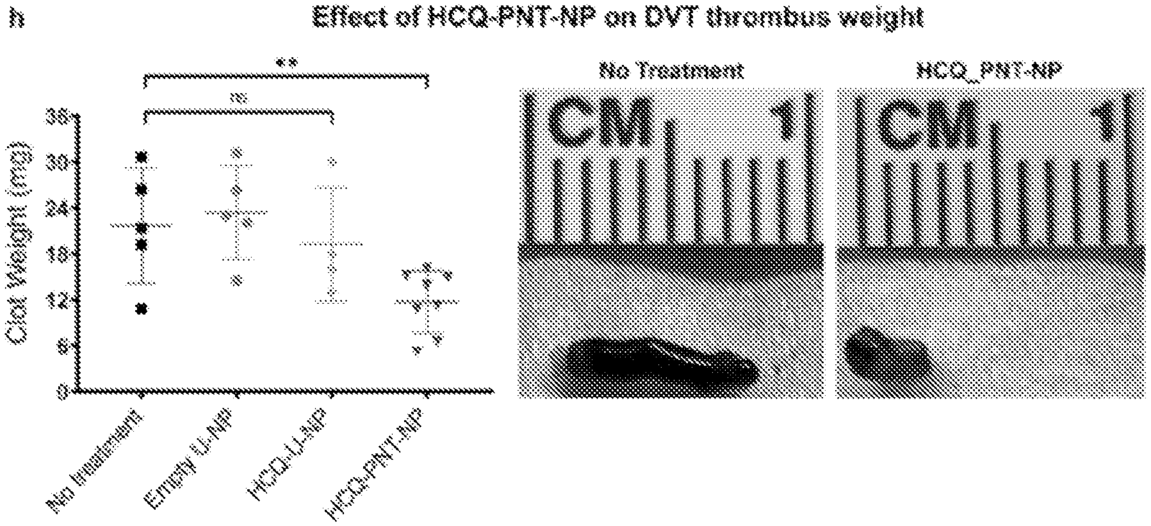

By way of example, FIG. 2 illustrates schematically a nanoparticle that includes P-selectin platelet targeting moieties spatially and topographically arranged on the nanoparticle surface along with neutrophil elastase binding peptides such that the neutrophil elastase binding peptides and platelet targeting moieties do not spatially mask each other and are able to adhere to an activated platelet surface with exposed surface receptors and enhance adhesion and retention of the nanoparticle to areas where activated neutrophils and activated platelets are present, such as areas of vascular injury In some embodiments, the P-selectin targeting peptides can have an amino acid sequence of EWVDV (SEQ ID NO: 60). In other embodiments, the P-selectin targeting peptide comprising an amino acid sequence of CDVEWVDVS (SEQ ID NO:61). In still other embodiments, the P-selectin targeting peptide can have an amino acid sequence of DAEWVDVS (SEQ ID NO: 62). The peptides may be synthesized by any method known in the art. For example, the P-selectin targeting peptides may be synthesized using Fmoc based solid phase chemistry and characterized using MALDI-TOF mass spectroscopy.

In other embodiments, the targeting moiety can be a targeting peptide comprising a tripeptide RGD (arginine-glycine-aspartic acid) amino acid sequence motif having a high selective affinity to GPIIb-IIIa. GPIIb-IIIa is an integrin upregulated and stimulated into a ligand-binding conformation on the surface of activated platelets. The RGD motif containing targeting peptide may contain a single repeat of the RGD motif or may contain multiple repeats of the RGD motif, such as, for example, 2, or 5, or 10 or more repeats of the RGD motif. One of skill in the art will understand that conservative substitutions of particular amino acid residues of the RGD motif containing targeting peptide may be used so long as the RGD motif containing targeting peptide retains the ability to bind comparably as the native RGD motif. One of skill in the art will also understand that conservative substitutions of particular amino acid residues flanking the RGD motif so long as the RGD motif containing targeting peptide retains the ability to bind comparably as the native RGD motif. A RGD peptide containing targeting moiety can be synthesized using FMoc-based solid phase chemistry on resin, and characterized using mass spectroscopy.

An RGD peptide having high selective affinity to GPIIb-IIIa can include a linear-RGD peptide or a cyclic RGD peptide. Preferred RGD peptides do not bind or activate quiescent platelets nor interact with other RGD-binding integrins. In some embodiments, the targeting moiety can include a linear RGD (lRGD) peptide. In some embodiments, the targeting moiety can include a cyclic RGD (abbreviated cRGD) peptide having the amino acid sequence of cyclo-CNPRGDY(-OEt)RC (SEQ ID NO: 63). For cRGD synthesis, the terminal cysteine residues of the linear precursor can be cyclized by a disulfide bond using a ferricyanide-mediated oxidation process.

In other embodiments, the nanoparticle or microparticle constructs can include endothelium targeting moieties that target inflamed endothelium surface molecules. Such targeting moieties can include antibodies, peptides or carbohydrate ligands directed to various cell adhesion molecules like ICAM, VCAM, PCAM, as well as integrins like αMβ3 and α5β1, and other lectins like E-selectin and L-selectin.

Other embodiments of targeting moieties include those that target cancer cells, such as peptides or antibodies that target or bind to PSMA, EGFR, Transferrin Receptor, HER-2 receptor, and/or Folate receptor.

It will be appreciated that any targeting moiety can be conjugated to the nanoparticle and/or microparticle constructs to facilitate targeting or delivery of the nanoparticle and/or microparticles constructs to sites of neutrophil activation.

The targeting moieties can be coupled to nanoparticles or microparticles of the composition using a linker as described herein. The linker can be of any suitable length and contain any suitable number of atoms and/or subunits. The linker can include one or a combination of chemical and/or biological moieties.

In some embodiments, the nanoparticle and/or microparticle constructs can further include imaging agents (or detectable moieties) and/or therapeutic agents that are encapsulated by (e.g., within liposome, lipidic nanoparticle or microparticle, or polymer nanoparticle or microparticle), contained in (e.g., polymer nanoparticles or dendrimers), or conjugated to the nanoparticles and/or microparticles.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and activated platelets in the subject. Examples of imaging agents include, but are not limited to: radionuclides, fluorescent dyes, chemiluminescent agents, colorimetric labels, and magnetic labels. In one example, the imaging agent can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as 19F.

In another example, the imaging agent can include an MRS/MRI radiolabel, such as gadolinium, $^{19}$F, $^{13}$C, that is coupled (e.g., attached or complexed) with the composition using general organic chemistry techniques. The imaging agent can also include radiolabels, such as $^{18}$F, $^{11}$C, $^{75}$Br, or $^{76}$Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The imaging can also include $^{123}$I for SPECT.

The imaging agent can further include known metal radiolabels, such as Technetium-99m ($^{99m}$Tc). Preparing radiolabeled derivatives of Tc99m is well known in the art. See, for example, Zhuang et al., "Neutral and stereospecific Tc-99m complexes: [$^{99m}$Tc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Therapeutic agents or bioactive agents, encapsulated by, contained in, and/or linked to nanoparticles or microparticles can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease, or injury in a subject. Examples of therapeutic agents include, but are not limited to thrombolytic, anti-thrombosis, and anti-proliferative agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

In some embodiments, the therapeutic agent can be a thrombolytic agent that is encapsulated by, contained in, and/or linked to the nanoparticles or microparticles. Thrombolytic agents are used to dissolve blood clots in a procedure termed thrombolysis and can limit the damage caused by the blockage or occlusion of a blood vessel. Thrombolytic agents can include analogs of tissue plasminogen activator (tPA), the protein that normally activates plasmin and recombinant tissue plasminogen activators (r-tPAs) include alteplase, reteplase, and tenecteplase (sold under the trade name TNKase) and desmoteplase. Additional thrombolytic agents include anistreplase (sold under the trade name EMINASE), streptokinase (sold under the trade names KABIKINASE, STREPTASE), and urokinase (sold under the trade name ABBOKINASE).

In some embodiments, the therapeutic agent can be an anti-thrombotic agent that is encapsulated by, contained in, and/or linked to the nanoparticles or microparticles. Anti-thrombotic agents can include anticoagulants and antiplatelet agents.

Anticoagulants slow down clotting, thereby reducing fibrin formation and preventing clots from forming and growing. Anticoagulants include coumarins (vitamin K antagonists) such as coumadin. Anticoagulants also include but are not limited to heparin, heparin derivatives and direct thrombin inhibitors including the bivalent drugs hirudin, lepirudin, and bivalirudin and the monovalent drugs argatroban and dabigatran.

Antiplatelet agents prevent platelets from clumping and also prevent clots from forming and growing. Antiplatelet agents can include but are not limited to aspirin and clopidogrel (sold under the trade name PLAVIX).

In other embodiments, the therapeutic agent can include NET-dissolving agents, such as DNAse, NET preventing agents, such as PAD-4 inhibitors, Akt-1 and Akt-2 phosphorylation inhibitors, inflammasome inhibitors, TLR 4 inhibitors, autophagy inhibitors, such as hydroxychloroquine (HCQ), heme quenchers, such as hemopexin, inhibitors of neutrophil FXII-uPAR interactions, and anticoagulant agents, such as heparin, enoxaparin, thrombin inhibitors, and other coagulation factor inhibitors).

In still other embodiments, the therapeutic agent can include an anti-cancer or an anti-proliferative agent that exerts an antineoplastic, chemotherapeutic, antiviral, anti-mitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and *vinca* alkaloids The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anticancer therapeutic agents that can be directly or indirectly linked to a targeting peptide in a molecular probe described herein include Taxol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer therapeutic agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G;

antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox TL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon;

leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; silicon phthalocyanine (PC4) sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosamOinoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other anti-cancer agents can include the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Arnad), AM-138 (Armad/ Kyowa Hakko), IDN-5005 (Indena), Cryptophycin 52 (also known as LY-355703), AC-7739 (Ajinomoto, also known as AVE-8063A and CS-39·HCl), AC-7700 (Ajinomoto, also known as AVE-8062, AVE-8062A, CS-39-L-Ser·HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (*Asta Medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (*Asta Medica*), D-68144 (*Asta Medica*), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (*Asta Medica*), D-68836 (*Asta Medica*), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-OY-007 (National Health Research Institutes), and SSR-250411 (Sanofi).

Still other anti-cancer therapeutic agents include alkylating agents, such as nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.), antimetabolites, such as folic acid analog (e.g., methotrexate), or pyrimidine analogs (e.g., fluorouracil, floxouridine, Cytarabine), purine analogs (e.g., mercaptopurine, thioguanine, pentostatin, *vinca* alkaloids (e.g., vinblastin, vincristine), epipodophyllotoxins (e.g., etoposide, teniposide), platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, amino glutethimide).

In some embodiments, cytotoxic compounds are included in a molecular agent described herein. Cytotoxic compounds include small-molecule drugs such as doxorubicin, mitoxantrone, methotrexate, and pyrimidine and purine analogs, referred to herein as antitumor agents.

In some embodiments, the therapeutic and/or imaging agents can be loaded into and/or onto the nanoparticles or microparticles by encapsulation, absorption, adsorption, and/or non-covalent linkage of the agent to or within the nanoparticle or microparticle. The amount of agent loaded onto or in the nanoparticle or microparticle can be controlled by changing the size of the nanoparticle or microparticle or the composition of the nanoparticle or microparticle.

In some embodiments, release of the therapeutic or imaging agent from the nanoparticle or microparticle of the composition can occur by desorption, diffusion through the polymer or lipid coating, or polymer or lipid wall, nanoparticle or microparticle erosion, and/or disruption of the nanoparticle or microparticle structure, which can all be controlled by the type of the nanoparticle or microparticle, i.e., having it become swollen or degradable in the chosen microenvironment.

In some embodiments, the therapeutic or imaging agent can be released from the nanoparticle or microparticle composition through the use of an internal and/or external trigger. Internal triggers include the body's internal pH, chemical and enzymatic activity. External triggers can include light and ultrasound.

In some embodiments, the compositions comprising a multi-ligand modified nanoparticle or microparticle described herein, can be formulated in a pharmaceutical composition and administered to an animal, preferably a human, to facilitate the delivery of a therapeutic agent.

Formulation of pharmaceutical composition for use in the modes of administration noted below (and others) are described, for example, in Remington's *Pharmaceutical Sciences* ($18^{th}$ edition), ed. A. Gennaro, 1990, Mack Publishing Company, Easton, Pa.

Such a pharmaceutical composition may consist of a plurality of surface modified nanoparticle or microparticle alone, in a form suitable for administration to a subject, or the pharmaceutical composition may comprise a plurality of nanoparticles and one or more pharmaceutically acceptable carriers, one or more additional ingredients, one or more pharmaceutically acceptable therapeutic agents, bioactive agents, imaging/diagnostic agents, or some combination of these. In some embodiments, the therapeutic agent may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the therapeutic agent may be combined and which, following the combination, can be used to administer the therapeutic agent to a subject. As used herein, the term "physiologically acceptable" ester or salt means an ester or salt form of the therapeutic agent which is compatible with any other ingredients of the pharmaceutical composition, which is not deleterious to the subject to which the composition is to be administered.

For example, pharmaceutical compositions can be in the form of a sterile aqueous or oily injectable solution containing, if desired, additional ingredients, for example, preservatives, buffers, tonicity agents, antioxidants, stabilizers, nonionic wetting or clarifying agents, and viscosity increasing agents. This suspension or solution may be formulated according to the known art, and may comprise, in addition to the therapeutic agent, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

In some embodiments, a bioactive agent, imaging/diagnostic agent, and/or therapeutic agent can be conjugated, encapsulated, and/or contained with the nanoparticle or microparticle constructs so that the nanoparticle or microparticle constructs act as a delivery vehicle. In other embodiments, the bioactive agent, imaging/diagnostic agent, and/or therapeutic agent can be merely contained in a pharmaceutical composition either with or without the nanoparticles and administered to concurrently with or separately from administration of the nanoparticles. Selection of a bioactive agent, imaging/diagnostic agent, and/or therapeutic agent to be conjugated to or encapsulated within the nanoparticle or microparticle is dependent upon the use of the nanoparticle or microparticle and/or the condition being treated and the site and route of administration.

In some embodiments, a composition including the nanoparticle and/or microparticle constructs and the neutrophil elastase binding peptides described herein can be used in a method of treating diseases caused by neutrophil activation and/or inflammatory diseases accompanied by neutrophil activation. The diseases caused by neutrophil activation and/or the inflammatory diseases accompanied by neutrophil activation can be one or a plurality of diseases selected from: (i) respiratory disorders, such as obstructive diseases of the airways including, such as asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha 1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome; (ii) skin disorders, such as psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; (iii) drug-induced disorders including fixed drug eruptions; ocular disorders, such as blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial; (iv) genitourinary disorders, such as nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female); (v) allograft rejection, such as acute and chronic following, for example, transplantation of kidney, heart, liver, lung, bone marrow, skin or cornea or following blood transfusion; or chronic graft versus host disease; (vi) other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome; (vii) oncology, such as treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes; and, (viii) infectious diseases, such as virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *Mycobacterium avium*, leprosy; and (ix) other infectious diseases, such as fungal diseases, chlamydia, Candida, aspergillus, cryptococcal meningitis, *Pneumocystis carnii*, cryptosporidiosis, histoplasmosis, toxoplasmosis, trypanosome infection and leishmaniasis.

In other embodiments, the diseases caused by neutrophil activation and/or the inflammatory diseases accompanied by neutrophil activation can be one or a plurality of diseases selected from venous and arterial thrombosis, deep vein thrombosis and vascular thrombo-embolism (DVT+VTE), lupus, psoriasis, atherosclerosis, endometriosis, trauma, sickle cell disease associated acute chest syndrome and pulmonary thrombosis, immunothrombosis, thrombo-inflammation, chronic and diabetic wounds, sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cancer, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, Kawasaki disease, multiple sclerosis, diabetic vascular complication, diabetic wounds, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, hemodialysis, extracorporeal circulation, artificial breathing, acute/chronic rejection after organ transplantation, SLE, rheumatoid arthritis, DIC, autoimmune disease group, Bechet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

It should be understood that the methods of treatment by the delivery of a composition including the nanoparticle or microparticle constructs includes the treatment of subjects that are already afflicted with a disease or symptoms thereof, as well as prophylactic treatment uses in subjects not yet afflicted and/or experiencing symptoms. In a preferred embodiment, the subject is an animal. In a more preferred embodiment, the subject is a human.

The compositions described herein can be delivered systematically (e.g., intravenously), regionally, or locally by, for example, intraarterial, intrathrombal, intravenous, parenteral, intraneural cavity, topical, oral, or local administration, as well as subcutaneous, intra-tracheal (e.g., by aerosol), or transmucosal (e.g., buccal, bladder, vaginal, uterine, rectal, nasal, mucosal). If delivery of the composition to the brain is desired, the targeted composition can be injected into an artery of the carotid system of arteries (e.g., occipital artery, auricular artery, temporal artery, cerebral artery, maxillary artery etc.). As discussed above, the composition can be formulated as a pharmaceutical composition for in vivo administration.

The pharmaceutical compositions described herein may also be formulated so as to provide slow, prolonged, or controlled release. In general, a controlled-release preparation is a pharmaceutical composition capable of releasing the nanoparticle and/or microparticle constructs at a desired or required rate to maintain constant activity for a desired or required period of time.

The relative amounts of the ingredients in a pharmaceutical composition of the invention will vary, depending upon the identity, size, and condition of the subject treated and further depending upon the route by which the composition is to be administered. By way of a non-limiting example, the composition may comprise between 0.1% and 100% (w/w) of the nanoparticle and/or microparticle constructs.

The composition including nanoparticle and/or microparticle constructs can be administered to the subject at an amount effective to provide a desired result(s) and to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The composition can be administered in a variety of unit dosage forms, depending upon the particular disease or disorder being treated, the general medical condition of each subject, the method of administration, and the like. Details on dosages are well described in the scientific literature. The exact amount and concentration of the targeted compositions, or the "effective dose", can be routinely determined (e.g., by a medical practitioner).

The pharmaceutical composition may be administered to a subject as needed. The pharmaceutical composition may be administered to a subject as frequently as several times daily, or it may be administered less frequently, such as once a day, once a week, once every two weeks, once a month, or even less frequently, such as once every several months or even once a year or less. The "dosing regimen" will depend upon a variety of factors, such as the type and severity of the disease being treated, the general state of the subject's health, the subject's age, and the like. Using guidelines describing alternative dosing regimens, e.g., from the use of other agents and compositions, the skilled artisan can readily determine by routine trials the optimal effective concentrations of the composition.

EXAMPLES

FIGS. 3(A-H) illustrate: (A) Neutrophil Elastase (NE) secretion from activated neutrophils and its stoichiometric inhibition by alpha-antitrypsin (AAT) radially distal from the neutrophil; (B) AAT binding to NE through reactive center loop (RCL); (C) Example of an RCL-derived NE binding peptide (NEBP); (D) HPLC-based analysis of NEBP interaction with mouse and human NE shows that such peptides are not cleaved by NE; (E) Surface Plasmon Resonance (SPR)-based analysis of NEBP binding to mouse NE (m-NE) shows high affinity binding; (F) Schematic of lipid conjugation to NEBP and to active platelet P-selectin binding peptide (PBP), and manufacture of nanoparticles with such lipopeptide systems to form neutrophil-targeted nanoparticle (NT-NP) and platelet-neutrophil-targeted nanoparticle (PNT-NP); (G) Dynamic Light Scattering (DLS) based size characterization of nanoparticles show diameter of ~150-200 nm; (H) SPR-based analysis of NT-NP binding to human NE (h-NE) shows high affinity of binding compared to untargeted nanoparticle (U-NP).

FIGS. 4(A-H) illustrate: (A) schematic of NT-NP binding to activated neutrophil; (B) NP effect on neutrophil viability shows that NT-NP is minimally toxic to neutrophils (similar to untargeted nanoparticle, U-NP); (C) Confocal fluorescence microscopy studies show that untargeted NP (U-NP) does not bind to inactive or activated fMLP-neutrophils, while NT-NP can specifically bind to fMLP-activated neutrophils (Blue: DAPI staining of neutrophil nucleus, Green: Neutrophil Elastase secreted from activated neutrophils, Red: Nanoparticles); (D) Flow cytometry analysis confirms enhanced binding of NT-NP to activated neutrophils (AN) compared to U-NP; (E) In vivo circulation time analysis by Rhodamine-B (RhB) fluorescence signal measurement in retro-orbitally drawn blood from mice injected with RhB-labeled U-NP and NT-NP show circulation half-life of NT-NP to be ~8 hrs; (F) In vivo studies in mice with LPS injection and neutrophil activation shows that NT-NP can bind to activated neutrophils in mouse retinal vasculature; (G) and (H): Quantitative analysis of NP co-localization with neutrophils in vivo confirms high co-localization of NT-NP with activated neutrophils, confirming specific targeting.

FIGS. 5(A-E) illustrate: (A) a schematic of PNT-NP binding to activated platelet-neutrophil (AP-AN complexes); (B) In vitro fluorescence-based studies with isolated neutrophils and platelets confirm that activated platelets and activated neutrophils form AP-AN complexes and PNT-NP can bind significantly more to these AP-AN complexes compared to untargeted nanoparticles (U-NP); (C) Quantitative fluorescence analysis from the above in vitro studies confirms significantly enhanced binding of PNT-NP to AP-AN complexes; (D) Flow cytometry analysis confirms that PNT-NP has significantly enhanced binding to activated neutrophils (AN) in AP-AN complexes; (E) Flow cytometry analysis confirms that PNT-NP has significantly enhanced binding to activated platelets (AP) in AP-AN complexes.

FIGS. 6(A-H) illustrate: (A) Schematic of microfluidic model of Deep Vein Thrombosis (DVT); (B) In vitro fluorescence-based studies under flow of human blood with fMLP-activated neutrophils and thrombin-activated platelets in the DVT microfluidic system shows enhanced binding of PNT-NP compared to U-NP to the thrombus forming in the 'valve pocket' of the microfluidic system (individual thrombus component fluorescence and NP fluorescence are labeled); (C) Using hydroxychloroquine (HCQ) as a model drug it is shown that 'free HCQ' affects neutrophil viability at and above $10^3$ ng/ml but when encapsulated within PNT-NP (HCQ-PNT-NP) the cell viability is maintained even at $10^7$ ng/ml, demonstrating that drug encapsulation within the PNT-NP enhances safety profile of the drug towards neutrophils; (D) HCQ_PNT-NP reduces neutrophil elastase (NE) activity from fMLP-activated neutrophils at levels similar to inhibition by AAT; (E) HCQ-PNT-NP reduces NETosis in fMLP-activated neutrophils reflected by the reduction in a characteristic NET marker, namely, citrullinated histone 3 (H3-C); (F) Intravenous administration of HCQ in mouse shows that administration of free HCQ results in high lethality while administration of HCQ-PNT-NP has minimum lethality, further signifying that drug encapsulation within PNT-NP improves drug safety profile in vivo; (G) Schematic of mouse inferior vena cava (JVC) ligation model of DVT; (H) Quantitative analysis as well as gross anatomical images of thrombi show that administration of HCQ_PNT-NP in mouse IVC DVT model reduces thrombus weight (and size), compared to HCQ_U-NP, signifying that targeted delivery of HCQ using PNT-NP as carrier platform results in significantly enhanced therapeutic effect.

From the above description of the invention, those skilled in the art will perceive improvements, changes, and modifications. Such improvements, changes, and modifications within the skill of the art are intended to be covered by the appended claims. All references, publications, and patents disclosed above are herein incorporated by reference in their entirety.

Having described the invention, we claim:

1. A composition comprising a plurality of nanoparticle and/or microparticle constructs that target activated neutrophils, each nanoparticle and/or microparticle construct having an outer surface and a plurality of targeting peptides conjugated to the surface of the nanoparticle and/or microparticle construct, wherein each of the targeting peptides comprising an amino acid sequence that has at least 60% identity to the amino acid sequence of SEQ ID NO: 1 and a substitution of an amino acid of at least one of residue 4P, 5M, or 6S of SEQ ID NO: 1 and wherein the targeting peptides bind neutrophil elastase on neutrophil surface.

2. The composition of claim 1, wherein the targeting peptide comprising an amino acid sequence that has at least 70% identity to the amino acid sequence of SEQ ID NO: 1 and a substitution of an amino acid of at least one of residue 4P, 5M, or 6S of SEQ ID NO: 1.

3. The composition of claim 1, wherein the targeting peptide includes an amino acid sequence of $EAIX_1X_2X_3IPPEVK$ (SEQ ID NO: 2), wherein $X_1$ is P, A, S, N, or L, $X_2$ is A, C, D, E, F, G, H, I, K, L, M, N, P, Q, R, S, T, W, or Y, $X_3$ is S or A, and at least one of $X_1$ is not P, $X_2$ is not M, or $X_3$ is not S.

4. The composition of claim 3, wherein $X_2$ is M, if at least one of $X_1$ or $X_3$ is not S.

5. The composition of claim 3, wherein $X_1$ is not P if $X_2$ is M and $X_3$ is S.

6. The composition of claim 3, wherein $X_2$ is not M if $X_1$ is P and $X_3$ is S.

7. The composition of claim 3, wherein $X_3$ is not S if $X_1$ is P and $X_2$ is M.

8. The composition of claim 1, the targeting peptide comprising an amino acid sequence selected from the group consisting of:

(SEQ ID NO: 3)
EAIPMAIPPEVKF, (SEQ ID NO: 4)
EAIPVSIPPEVKF, (SEQ ID NO: 5)
EAIPASIPPEVKF, (SEQ ID NO: 6)
EAIPCSIPPEVKF, (SEQ ID NO: 7)
EAIPDSIPPEVKF, (SEQ ID NO: 8)
EAIPESIPPEVKF, (SEQ ID NO: 9)
EAIPFSIPPEVKF, (SEQ ID NO: 10)
EAIPGSIPPEVKF, (SEQ ID NO: 11)
EAIPHSIPPEVKF, (SEQ ID NO: 12)
EAIPISIPPEVKF, (SEQ ID NO: 13)
EAIPKSIPPEVKF, (SEQ ID NO: 14)
EAIPLSIPPEVKF, (SEQ ID NO: 15)
EAIPNSIPPEVKF, (SEQ ID NO: 16)
EAIPPSIPPEVKF, (SEQ ID NO: 17)
EAIPQSIPPEVKF, (SEQ ID NO: 18)
EAIPRSIPPEVKF, (SEQ ID NO: 19)
EAIPSSIPPEVKF, (SEQ ID NO: 20)
EAIPTSIPPEVKF, (SEQ ID NO: 21)
EAIPWSIPPEVKF, (SEQ ID NO: 22)
EAIPYSIPPEVKF, (SEQ ID NO: 23)
EAIAMSIPPEVKF, (SEQ ID NO: 24)
EAISMSIPPEVKF, (SEQ ID NO: 25)
EAINMSIPPEVKF, (SEQ ID NO: 26)
EAILMSIPPEVKF, (SEQ ID NO: 27)
EAIAMAIPPEVKF,

-continued (SEQ ID NO: 28)
EAISMAIPPEVKF, (SEQ ID NO: 29)
EAINMAIPPEVKF, (SEQ ID NO: 30)
EAILMAIPPEVKF, (SEQ ID NO: 31)
EAIPMAIPPEVK, (SEQ ID NO: 32)
EAIPVSIPPEVK, (SEQ ID NO: 33)
EAIPASIPPEVK, (SEQ ID NO: 34)
EAIPCSIPPEVK, (SEQ ID NO: 35)
EAIPDSIPPEVK, (SEQ ID NO: 36)
EAIPESIPPEVK, (SEQ ID NO: 37)
EAIPFSIPPEVK, (SEQ ID NO: 38)
EAIPGSIPPEVK, (SEQ ID NO: 39)
EAIPHSIPPEVK, (SEQ ID NO: 40)
EAIPISIPPEVK, (SEQ ID NO: 41)
EAIPKSIPPEVK, (SEQ ID NO: 42)
EAIPLSIPPEVK, (SEQ ID NO: 43)
EAIPNSIPPEVK, (SEQ ID NO: 44)
EAIPPSIPPEVK, (SEQ ID NO: 45)
EAIPQSIPPEVK, (SEQ ID NO: 46)
EAIPRSIPPEVK, (SEQ ID NO: 47)
EAIPSSIPPEVK, (SEQ ID NO: 48)
EAIPTSIPPEVK, (SEQ ID NO: 49)
EAIPWSIPPEVK, (SEQ ID NO: 50)
EAIPYSIPPEVK, (SEQ ID NO: 51)
EAIAMSIPPEVK, (SEQ ID NO: 52)
EAISMSIPPEVK, (SEQ ID NO: 53)
EAINMSIPPEVK, (SEQ ID NO: 54)
EAILMSIPPEVK, -continued (SEQ ID NO: 55)
EAIAMAIPPEVK, (SEQ ID NO: 56)
EAISMAIPPEVK, (SEQ ID NO: 57)
EAINMAIPPEVK, (SEQ ID NO: 58)
EAILMAIPPEVK.

9. The composition of claim 1, wherein the targeting peptide includes CG residues linked to the N-terminal E residue (1E) of the amino acid sequence that links the targeting peptide to a polyethylene glycol (PEG) linker conjugated to the surface of the nanoparticle and/or microparticle construct.

10. The composition of claim 1, the nanoparticle and/or microparticle construct comprising a liposome.

11. The composition of claim 1, the nanoparticle and/or microparticle construct further comprising a therapeutic agent, wherein the therapeutic agent is encapsulated by and/or conjugated to the nanoparticle and/or microparticle construct.

12. The composition of claim 1, wherein targeting peptides are spatially or topographically arranged on the surfaces of the nanoparticle and/or microparticle constructs such that the targeting peptides do not spatially mask each other.

13. The composition of claim 1, wherein the nanoparticle and/or microparticle construct further comprises additional targeting peptide conjugated to the surface of the nanoparticle and/or microparticle construct that is different than the targeting peptide of an amino acid sequence that has at least 60% identity to SEQ ID NO: 1.

14. The composition of claim 13, wherein the other targeting peptides include platelet targeting peptides, cancer cell targeting peptides, and immune cell targeting peptides.

15. The composition of claim 14, the platelet targeting peptide including a glycoprotein IIb-IIIa (GPIIb-IIIa)-binding peptide and/or a p-selectin binding peptide.

16. The composition of claim 14, the cancer cell targeting peptide comprising a PSMA targeting peptide and/or EGFR targeting peptide.

17. The composition of claim 1, for treating diseases caused by neutrophil activation and/or inflammatory diseases accompanied by neutrophil activation.

18. The composition of claim 17, wherein the diseases caused by neutrophil activation and/or the inflammatory diseases accompanied by neutrophil activation are one or a plurality of thrombotic disorders vascular diseases selected from venous thrombosis, arterial thrombosis, deep vein thrombosis (DVT), vascular thrombo-embolism VTE), atherosclerosis, pulmonary thrombosis, diabetic vascular complication, arteriosclerosis, and disseminated intravascular coagulation (DIC).

* * * * *

SEQUENCE LISTING

```
<160> NUMBER OF SEQ ID NOS: 67

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Glu Ala Ile Pro Met Ser Ile Pro Pro Glu Val Lys
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: (4)..(4)
<223> OTHER INFORMATION: X1 is P, A, S, N, or L
<220> FEATURE:
<221> NAME/KEY: SITE
<222> LOCATION: (5)..(5)
<223> OTHER INFORMATION: X2 is A, C, D, E, F, G, H, I, K, L, M, N, P, Q,
      R, S, T, W, or Y
<220> FEATURE:
<221> NAME/KEY: SITE
<222> LOCATION: (6)..(6)
<223> OTHER INFORMATION: X3 is S or A

<400> SEQUENCE: 2
```

```
Glu Ala Ile Xaa Xaa Xaa Ile Pro Pro Glu Val Lys
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Glu Ala Ile Pro Met Ala Ile Pro Pro Glu Val Lys Phe
1               5                   10


<210> SEQ ID NO 4
<211> LENGTH: 13
<212> TYPE: PRT
<213> ORGANISM: Artificial Sequence
<220> FEATURE:
<223> OTHER INFORMATION: Synthetic Construct

<400> SEQUENCE: 4

Glu Ala Ile Pro Val Ser Ile Pro Pro Glu Val Lys Phe
1               5                   10


<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Glu Ala Ile Pro Ala Ser Ile Pro Pro Glu Val Lys Phe
1               5                   10


<210> SEQ ID NO 6
<211> LENGTH: 13
<212> TYPE: PRT
<213> ORGANISM: Artificial Sequence
<220> FEATURE:
<223> OTHER INFORMATION: Synthetic Construct

<400> SEQUENCE: 6

Glu Ala Ile Pro Cys Ser Ile Pro Pro Glu Val Lys Phe
1               5                   10


<210> SEQ ID NO 7
<211> LENGTH: 13
<212> TYPE: PRT
<213> ORGANISM: Artificial Sequence
<220> FEATURE:
<223> OTHER INFORMATION: Synthetic Construct

<400> SEQUENCE: 7

Glu Ala Ile Pro Asp Ser Ile Pro Pro Glu Val Lys Phe
1               5                   10


<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8
```

Glu Ala Ile Pro Glu Ser Ile Pro Pro Glu Val Lys Phe
1 5 10

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

Glu Ala Ile Pro Phe Ser Ile Pro Pro Glu Val Lys Phe
1 5 10

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Glu Ala Ile Pro Gly Ser Ile Pro Pro Glu Val Lys Phe
1 5 10

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct

<400> SEQUENCE: 11

Glu Ala Ile Pro His Ser Ile Pro Pro Glu Val Lys Phe
1 5 10

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Glu Ala Ile Pro Ile Ser Ile Pro Pro Glu Val Lys Phe
1 5 10

<210> SEQ ID NO 13
<211> LENGTH: 13
<212> TYPE: PRT
<213> ORGANISM: Artificial Sequence
<220> FEATURE:
<223> OTHER INFORMATION: Synthetic Construct

<400> SEQUENCE: 13

Glu Ala Ile Pro Lys Ser Ile Pro Pro Glu Val Lys Phe
1 5 10

<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

Glu Ala Ile Pro Leu Ser Ile Pro Pro Glu Val Lys Phe 1 5 10

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Glu Ala Ile Pro Asn Ser Ile Pro Pro Glu Val Lys Phe
1 5 10

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Glu Ala Ile Pro Pro Ser Ile Pro Pro Glu Val Lys Phe
1 5 10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct

<400> SEQUENCE: 17

Glu Ala Ile Pro Gln Ser Ile Pro Pro Glu Val Lys Phe
1 5 10

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Glu Ala Ile Pro Arg Ser Ile Pro Pro Glu Val Lys Phe
1 5 10

<210> SEQ ID NO 19
<211> LENGTH: 13
<212> TYPE: PRT
<213> ORGANISM: Artificial Sequence
<220> FEATURE:
<223> OTHER INFORMATION: Synthetic Construct

<400> SEQUENCE: 19

Glu Ala Ile Pro Ser Ser Ile Pro Pro Glu Val Lys Phe
1 5 10

<210> SEQ ID NO 20
<211> LENGTH: 13
<212> TYPE: PRT
<213> ORGANISM: Artificial Sequence
<220> FEATURE:
<223> OTHER INFORMATION: Synthetic Construct

<400> SEQUENCE: 20

Glu Ala Ile Pro Thr Ser Ile Pro Pro Glu Val Lys Phe
1 5 10

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

Glu Ala Ile Pro Trp Ser Ile Pro Pro Glu Val Lys Phe
1 5 10

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Glu Ala Ile Pro Tyr Ser Ile Pro Pro Glu Val Lys Phe
1 5 10

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

Glu Ala Ile Ala Met Ser Ile Pro Pro Glu Val Lys Phe
1 5 10

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct

<400> SEQUENCE: 24

Glu Ala Ile Ser Met Ser Ile Pro Pro Glu Val Lys Phe
1 5 10

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Glu Ala Ile Asn Met Ser Ile Pro Pro Glu Val Lys Phe
1 5 10

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26

Glu Ala Ile Leu Met Ser Ile Pro Pro Glu Val Lys Phe
1 5 10

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Glu Ala Ile Ala Met Ala Ile Pro Pro Glu Val Lys Phe
1 5 10

<210> SEQ ID NO 28
<211> LENGTH: 13
<212> TYPE: PRT
<213> ORGANISM: Artificial Sequence
<220> FEATURE:
<223> OTHER INFORMATION: Synthetic Construct

<400> SEQUENCE: 28

Glu Ala Ile Ser Met Ala Ile Pro Pro Glu Val Lys Phe
1 5 10

<210> SEQ ID NO 29
<211> LENGTH: 13
<212> TYPE: PRT
<213> ORGANISM: Artificial Sequence
<220> FEATURE:
<223> OTHER INFORMATION: Synthetic Construct

<400> SEQUENCE: 29

Glu Ala Ile Asn Met Ala Ile Pro Pro Glu Val Lys Phe
1 5 10

<210> SEQ ID NO 30
<211> LENGTH: 13
<212> TYPE: PRT
<213> ORGANISM: Artificial Sequence
<220> FEATURE:
<223> OTHER INFORMATION: Synthetic Construct

<400> SEQUENCE: 30

Glu Ala Ile Leu Met Ala Ile Pro Pro Glu Val Lys Phe
1 5 10

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Glu Ala Ile Pro Met Ala Ile Pro Pro Glu Val Lys
1 5 10

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32

Glu Ala Ile Pro Val Ser Ile Pro Pro Glu Val Lys
1 5 10

<210> SEQ ID NO 33
<211> LENGTH: 12
<212> TYPE: PRT
<213> ORGANISM: Artificial Sequence
<220> FEATURE:
<223> OTHER INFORMATION: Synthetic Construct

<400> SEQUENCE: 33

Glu Ala Ile Pro Ala Ser Ile Pro Pro Glu Val Lys
1 5 10

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Glu Ala Ile Pro Cys Ser Ile Pro Pro Glu Val Lys
1 5 10

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Glu Ala Ile Pro Asp Ser Ile Pro Pro Glu Val Lys
1 5 10

<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

<400> SEQUENCE: 36

Glu Ala Ile Pro Glu Ser Ile Pro Pro Glu Val Lys
1 5 10

<210> SEQ ID NO 37
<211> LENGTH: 12
<212> TYPE: PRT
<213> ORGANISM: Artificial Sequence
<220> FEATURE:
<223> OTHER INFORMATION: Synthetic Construct

<400> SEQUENCE: 37

Glu Ala Ile Pro Phe Ser Ile Pro Pro Glu Val Lys
1 5 10

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Glu Ala Ile Pro Gly Ser Ile Pro Pro Glu Val Lys
1 5 10

<210> SEQ ID NO 39

<211> LENGTH: 12
<212> TYPE: PRT
<213> ORGANISM: Artificial Sequence
<220> FEATURE:
<223> OTHER INFORMATION: Synthetic Construct

<400> SEQUENCE: 39

Glu Ala Ile Pro His Ser Ile Pro Pro Glu Val Lys
1 5 10

<210> SEQ ID NO 40
<211> LENGTH: 12
<212> TYPE: PRT
<213> ORGANISM: Artificial Sequence
<220> FEATURE:
<223> OTHER INFORMATION: Syntethic Construct

<400> SEQUENCE: 40

Glu Ala Ile Pro Ile Ser Ile Pro Pro Glu Val Lys
1 5 10

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct

<400> SEQUENCE: 41

Glu Ala Ile Pro Lys Ser Ile Pro Pro Glu Val Lys
1 5 10

<210> SEQ ID NO 42
<211> LENGTH: 12
<212> TYPE: PRT
<213> ORGANISM: Artificial Sequence
<220> FEATURE:
<223> OTHER INFORMATION: Synthetic Construct

<400> SEQUENCE: 42

Glu Ala Ile Pro Leu Ser Ile Pro Pro Glu Val Lys
1 5 10

<210> SEQ ID NO 43
<211> LENGTH: 12
<212> TYPE: PRT
<213> ORGANISM: Artificial Sequence
<220> FEATURE:
<223> OTHER INFORMATION: Synthetic Construct

<400> SEQUENCE: 43

Glu Ala Ile Pro Asn Ser Ile Pro Pro Glu Val Lys
1 5 10

<210> SEQ ID NO 44
<211> LENGTH: 12
<212> TYPE: PRT
<213> ORGANISM: Artificial Sequence
<220> FEATURE:
<223> OTHER INFORMATION: Synthetic Construct

<400> SEQUENCE: 44

Glu Ala Ile Pro Pro Ser Ile Pro Pro Glu Val Lys
1 5 10

<210> SEQ ID NO 45
<211> LENGTH: 12

<212> TYPE: PRT
<213> ORGANISM: Artificial Sequence
<220> FEATURE:
<223> OTHER INFORMATION: Synthetic Construct

<400> SEQUENCE: 45

Glu Ala Ile Pro Gln Ser Ile Pro Pro Glu Val Lys
1 5 10

<210> SEQ ID NO 46
<211> LENGTH: 12
<212> TYPE: PRT
<213> ORGANISM: Artificial Sequence
<220> FEATURE:
<223> OTHER INFORMATION: Synthetic Construct

<400> SEQUENCE: 46

Glu Ala Ile Pro Arg Ser Ile Pro Pro Glu Val Lys
1 5 10

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

Glu Ala Ile Pro Ser Ser Ile Pro Pro Glu Val Lys
1 5 10

<210> SEQ ID NO 48
<211> LENGTH: 12
<212> TYPE: PRT
<213> ORGANISM: Artificial Sequence
<220> FEATURE:
<223> OTHER INFORMATION: Synthetic Construct

<400> SEQUENCE: 48

Glu Ala Ile Pro Thr Ser Ile Pro Pro Glu Val Lys
1 5 10

<210> SEQ ID NO 49
<211> LENGTH: 12
<212> TYPE: PRT
<213> ORGANISM: Artificial Sequence
<220> FEATURE:
<223> OTHER INFORMATION: Synthetic Construct

<400> SEQUENCE: 49

Glu Ala Ile Pro Trp Ser Ile Pro Pro Glu Val Lys
1 5 10

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Glu Ala Ile Pro Tyr Ser Ile Pro Pro Glu Val Lys
1 5 10

<210> SEQ ID NO 51
<211> LENGTH: 12
<212> TYPE: PRT

<213> ORGANISM: Artificial Sequence
<220> FEATURE:
<223> OTHER INFORMATION: Synthetic Construct

<400> SEQUENCE: 51

Glu Ala Ile Ala Met Ser Ile Pro Pro Glu Val Lys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Construct

<400> SEQUENCE: 52

Glu Ala Ile Ser Met Ser Ile Pro Pro Glu Val Lys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Construct

<400> SEQUENCE: 53

Glu Ala Ile Asn Met Ser Ile Pro Pro Glu Val Lys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Construct

<400> SEQUENCE: 54

Glu Ala Ile Leu Met Ser Ile Pro Pro Glu Val Lys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Glu Ala Ile Ala Met Ala Ile Pro Pro Glu Val Lys
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Construct

<400> SEQUENCE: 56

Glu Ala Ile Ser Met Ala Ile Pro Pro Glu Val Lys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic Construct

<400> SEQUENCE: 57

Glu Ala Ile Asn Met Ala Ile Pro Pro Glu Val Lys
1 5 10

<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

Glu Ala Ile Leu Met Ala Ile Pro Pro Glu Val Lys
1 5 10

<210> SEQ ID NO 59
<211> LENGTH: 13
<212> TYPE: PRT
<213> ORGANISM: Artificial Sequence
<220> FEATURE:
<223> OTHER INFORMATION: Synthetic Construct

<400> SEQUENCE: 59

Glu Ala Ile Pro Met Ser Ile Pro Pro Glu Val Lys Phe
1 5 10

<210> SEQ ID NO 60
<211> LENGTH: 5
<212> TYPE: PRT
<213> ORGANISM: Artificial Sequence
<220> FEATURE:
<223> OTHER INFORMATION: Synthetic Construct

<400> SEQUENCE: 60

Glu Trp Val Asp Val
1 5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Cys Asp Val Glu Trp Val Asp Val Ser
1 5

<210> SEQ ID NO 62
<211> LENGTH: 8
<212> TYPE: PRT
<213> ORGANISM: Artificial Sequence
<220> FEATURE:
<223> OTHER INFORMATION: Synthetic Construct

<400> SEQUENCE: 62

Asp Ala Glu Trp Val Asp Val Ser
1 5

<210> SEQ ID NO 63
<211> LENGTH: 9
<212> TYPE: PRT
<213> ORGANISM: Artificial Sequence
<220> FEATURE:

-continued

```
<223> OTHER INFORMATION: Synthetic Construct

<400> SEQUENCE: 63

Cys Asn Pro Arg Gly Asp Tyr Arg Cys
1               5


<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

Cys Gly Glu Ala Ile Pro Met Ser Ile Pro Pro Glu Val Lys
1               5                   10


<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Cys Asp Ala Glu Trp Val Asp Val Ser
1               5


<210> SEQ ID NO 66
<211> LENGTH: 14
<212> TYPE: PRT
<213> ORGANISM: Artificial Sequence
<220> FEATURE:
<223> OTHER INFORMATION: Synthetic Construct

<400> SEQUENCE: 66

Cys Gly Glu Ala Ile Pro Met Ser Ile Pro Pro Glu Val Lys
1               5                   10


<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Cys Asp Ala Glu Trp Val Asp Val Ser
1               5
```